(12) United States Patent
Bateman et al.

(10) Patent No.: US 9,012,840 B2
(45) Date of Patent: Apr. 21, 2015

(54) MASS SPECTROMETER

(75) Inventors: Robert Harold Bateman, Cheshire (GB); Kevin Giles, Cheshire (GB)

(73) Assignee: Micromass UK Limited, Wilmslow (GB)

( * ) Notice: Subject to any disclaimer, the term of this patent is extended or adjusted under 35 U.S.C. 154(b) by 2440 days.

(21) Appl. No.: 11/720,771

(22) PCT Filed: Dec. 7, 2005

(86) PCT No.: PCT/GB2005/004672
§ 371 (c)(1),
(2), (4) Date: Dec. 29, 2009

(87) PCT Pub. No.: WO2006/061593
PCT Pub. Date: Jun. 15, 2006

(65) Prior Publication Data
US 2010/0108878 A1    May 6, 2010

Related U.S. Application Data

(60) Provisional application No. 60/637,835, filed on Dec. 21, 2004.

(30) Foreign Application Priority Data

Dec. 7, 2004  (GB) .................................. 0426778.7
May 27, 2005 (GB) .................................. 0510914.5

(51) Int. Cl.
*H01J 49/26* (2006.01)
*H01J 49/06* (2006.01)
*G01N 27/62* (2006.01)
*H01J 49/00* (2006.01)

(52) U.S. Cl.
CPC ............ *H01J 49/062* (2013.01); *G01N 27/622* (2013.01); *H01J 49/004* (2013.01)

(58) Field of Classification Search
USPC .......... 250/281, 282, 283, 290, 291, 292, 293
See application file for complete search history.

(56) References Cited

U.S. PATENT DOCUMENTS

| | | | |
|---|---|---|---|
| 3,845,301 A | 10/1974 | Wernlund et al. | |
| 6,111,250 A | 8/2000 | Thomson et al. | |
| 6,630,662 B1 | 10/2003 | Loboda | |
| 6,914,241 B2 | 7/2005 | Giles et al. | |
| 7,196,324 B2 | 3/2007 | Verentchikov | |
| 7,205,538 B2 | 4/2007 | Bateman et al. | |
| 2003/0001084 A1* | 1/2003 | Bateman et al. ............ | 250/281 |
| 2003/0001088 A1* | 1/2003 | Bateman et al. ............ | 250/287 |
| 2003/0020012 A1 | 1/2003 | Guevremont | |
| 2003/0209665 A1 | 11/2003 | Losch et al. | |
| 2003/0213900 A1 | 11/2003 | Hoyes | |

(Continued)

FOREIGN PATENT DOCUMENTS

| EP | 1267387 | 4/2005 |
|---|---|---|
| GB | 2389704 | 12/2003 |

(Continued)

*Primary Examiner* — Nicole Ippolito
(74) *Attorney, Agent, or Firm* — Diederiks & Whitelaw, PLC

(57) ABSTRACT

A mass spectrometer is disclosed comprising a first quadrupole rod set mass filter, a collision cell, an ion mobility spectrometer or separator, an ion guide or collision cell arranged downstream of the ion mobility spectrometer or separator, a second quadrupole rod set mass filter and an ion detector.

42 Claims, 7 Drawing Sheets

(56) References Cited

U.S. PATENT DOCUMENTS

| | | |
|---|---|---|
| 2004/0026613 A1 | 2/2004 | Bateman et al. |
| 2004/0026614 A1 | 2/2004 | Bateman et al. |
| 2004/0094702 A1* | 5/2004 | Clemmer .............. 250/283 |
| 2004/0149902 A1 | 8/2004 | Park |
| 2004/0188603 A1 | 9/2004 | Bateman et al. |
| 2005/0189486 A1* | 9/2005 | Fuhrer et al. .......... 250/287 |
| 2006/0192104 A1* | 8/2006 | Schultz et al. ......... 250/287 |

FOREIGN PATENT DOCUMENTS

| | | |
|---|---|---|
| GB | 2421839 | 7/2006 |
| GB | 2421840 | 7/2006 |
| GB | 2421842 | 7/2006 |
| GB | 2423628 | 8/2006 |
| JP | S5033895 | 4/1975 |
| WO | WO 02/07185 | 1/2002 |
| WO | WO 02/086946 | 10/2002 |
| WO | WO 2005/114703 | 12/2005 |

* cited by examiner

MASS SPECTROMETER

CROSS REFERENCE TO RELATED APPLICATIONS

This application is the National Stage of International Application No. PCT/GB2005/004672, filed on Dec. 7, 2005, which claims priority to and benefit of U.S. Provisional Patent Application Ser. No. 60/637,835, filed on Dec. 21, 2004, and priority to and benefit of United Kingdom Patent Application Nos. 0426778, filed Dec. 7, 2004, and U.S. Pat. No. 0,510,914, filed May 27, 2005. The entire contents of these applications are incorporated herein by reference.

BACKGROUND OF THE INVENTION

The present invention relates to a mass spectrometer and a method of mass spectrometry.

Tandem mass spectrometry, or MS/MS, has become the preferred technology for many applications in which mass spectrometry plays a part. Tandem mass spectrometry allows selection and isolation of specific compounds of interest and their subsequent identification. The extra selectivity of MS/MS enables this technology to be used for quantification of target compounds even in the presence of complex matrices.

Tandem mass spectrometers are known which comprise a mass filter, a collision cell arranged downstream of the mass filter which fragments selected parent or precursor ions, and a mass analyser which mass analyses the fragment or daughter ions which emerge from the collision cell. Ions are fragmented in the collision cell by Collision Induced Decomposition ("CID") wherein ions undergo multiple collisions with gas molecules in the partially enclosed collision cell.

In most tandem mass spectrometers the processes of selecting specific parent or precursor ions, fragmenting the selected parent or precursor ions and mass analysing the resulting fragment or daughter ions takes place sequentially in space. The mass filter may be used to select parent or precursor ions of a target compound. The parent or precursor ions are then passed to a collision cell which fragments those parent or precursor ions. The mass analyser is then used to mass analyse the resulting fragment or daughter ions.

One known tandem mass spectrometer is commonly referred to as a triple quadrupole mass spectrometer. Triple quadrupole mass spectrometers comprise a first quadrupole rod set mass filter or mass analyser followed by a collision cell. A second quadrupole rod set mass filter or mass analyser is arranged downstream of the collision cell followed by an ion detector. The name triple quadrupole is derived from the first such instrument wherein an RF quadrupole was used to guide ions through the collision cell.

The first quadrupole rod set mass filter is typically used to select parent or precursor ions having a specific mass to charge ratio. Therefore, in order to record a full mass spectrum, the first quadrupole rod set mass filter must be scanned across the full mass to charge ratio range in order to sequentially transmit ions having different mass to charge ratios. The duty cycle for this process is relatively low and as a consequence the sensitivity of a quadrupole rod set mass filter when used to record a full mass spectrum is relatively poor. On the other hand, the quadrupole mass filter will have 100% duty cycle when used to transmit ions having a specific mass to charge ratio.

A triple quadrupole mass spectrometer may be used for Selected Reaction Monitoring ("SRM") experiments wherein parent or precursor ions having a specific mass to charge ratio are arranged to be transmitted by the first quadrupole rod set mass filter arranged upstream of the collision cell. The specific parent or precursor ions are then transmitted to the collision cell and are fragmented thereby forming fragment or daughter ions. The second mass filter is arranged so as to transmit fragment or daughter ions having a specific mass to charge ratio. This arrangement is very specific and exceptionally sensitive. Triple quadrupole mass spectrometers have found significant use in the drug discovery and development process where they are used both for Selected Reaction Monitoring experiments and also for Multiple Reaction Monitoring ("MRM") experiments to quantify target compounds of biological significance.

A limitation of conventional triple quadrupole mass spectrometers becomes evident when a conventional mass spectrometer is attempted to be used in a Multiple Reaction Monitoring (MRM) mode to monitor many different transitions or reactions. For each additional reaction that is included in an experiment, there is a corresponding reduction in the sampling duty cycle for each reaction monitored. For confirmation or validation of certain quantification analyses it is desirable to monitor several reactions. Indeed, for some applications it is a regulatory requirement to monitor several reactions in order to confirm or validate the quantification analysis.

A common application in peptide and protein analysis for a triple quadrupole mass spectrometer makes use of a parent or precursor ion scanning mode of operation. In this mode of operation the second mass filter or mass analyser arranged downstream of the collision cell is set so as to transmit only a specific characteristic fragment or daughter ion. The first mass filter arranged upstream of the collision cell is scanned so as to sequentially transmit different parent or precursor ions to the collision cell for subsequent fragmentation. When a specific fragment or daughter ion is detected then the mass to charge ratio of the corresponding parent or precursor ions which were transmitted by the first mass filter upstream of the collision cell are recorded. This approach has proved particularly useful in the analysis of protein post-translational modifications such as phosphorylation and glycosylation. However, since it is necessary to scan the first quadrupole mass filter upstream of the collision cell then the sampling duty cycle can be quite low, commonly less than 1%, and consequently the sensitivity is also relatively low.

It is therefore desired to provide an improved mass spectrometer and method of mass spectrometry which does not suffer from some or all of the disadvantages of the prior art.

SUMMARY OF THE INVENTION

According to an aspect of the present invention there is provided a mass spectrometer comprising:

a first ion guide or a first collision, fragmentation or reaction device arranged and adapted to fragment or react ions and to produce product, daughter, adduct or fragment ions; and an ion mobility spectrometer or separator arranged downstream of the first ion guide or the first collision, fragmentation or reaction device, the ion mobility spectrometer or separator being arranged to temporally separate product, daughter, adduct or fragment ions according to their ion mobility which emerge from or which have been transmitted from the first ion guide or the first collision, fragmentation or reaction device.

Ions are preferably fragmented or reacted in the collision fragmentation or reaction device and the resulting fragment, daughter, product or adduct ions are then preferably temporally separated in an ion mobility spectrometer or separator and are preferably detected by an ion detector.

According to an embodiment the collision, fragmentation or reaction device may be arranged and adapted to fragment ions by Collision Induced Dissociation ("CID"). According to this embodiment, ions may be accelerated such that they have a relatively high kinetic energy when they enter the device that they are caused to fragment into fragment or daughter ions upon colliding with gas molecules in the device. Alternatively and/or additionally, ions may accelerated within the device such that they collide energetically with background gas molecules within the device and fragment into fragment or daughter ions.

Alternatively, the collision, fragmentation or reaction device may selected from the group consisting of: (i) a Surface Induced Dissociation ("SID") fragmentation device; (ii) an Electron Transfer Dissociation fragmentation device; (iii) an Electron Capture Dissociation fragmentation device; (iv) an Electron Collision or Impact Dissociation fragmentation device; (v) a Photo Induced Dissociation ("PID") fragmentation device; (vi) a Laser Induced Dissociation fragmentation device; (vii) an infrared radiation induced dissociation device; (viii) an ultraviolet radiation induced dissociation device; (ix) a nozzle-skimmer interface fragmentation device; (x) an in-source fragmentation device; (xi) an ion-source Collision Induced Dissociation fragmentation device; (xii) a thermal or temperature source fragmentation device; (xiii) an electric field induced fragmentation device; (xiv) a magnetic field induced fragmentation device; (xv) an enzyme digestion or enzyme degradation fragmentation device; (xvi) an ion-ion reaction fragmentation device; (xvii) an ion-molecule reaction fragmentation device; (xviii) an ion-atom reaction fragmentation device; (xix) an ion-metastable ion reaction fragmentation device; (xx) an ion-metastable molecule reaction fragmentation device; (xxi) an ion-metastable atom reaction fragmentation device; (xxii) an ion-ion reaction device for reacting ions to form adduct or product ions; (xxiii) an ion-molecule reaction device for reacting ions to form adduct or product ions; (xxiv) an ion-atom reaction device for reacting ions to form adduct or product ions; (xxv) an ion-metastable ion reaction device for reacting ions to form adduct or product ions; (xxvi) an ion-metastable molecule reaction device for reacting ions to form adduct or product ions; and (xxvii) an ion-metastable atom reaction device for reacting ions to form adduct or product ions.

A reaction device should be understood as comprising a device wherein ions, atoms or molecules are rearranged or reacted so as to form a new species of ion, atom or molecule. An X-Y reaction fragmentation device should be understood as meaning a device wherein X and Y combine to form a product which then fragments. This is different to a fragmentation device per se wherein ions may be caused to fragment without first forming a product. An X-Y reaction device should be understood as meaning a device wherein X and Y combine to form a product and wherein the product does not necessarily then fragment.

The collision, fragmentation or reaction device may be arranged and adapted to trap ions within the collision, fragmentation or reaction device in a mode of operation.

According to an embodiment the collision, fragmentation or reaction device is arranged and adapted to pulse ions out of the collision, fragmentation or reaction device and into or towards the ion mobility spectrometer or separator.

The mass spectrometer preferably further comprises a mass filter or mass analyser arranged upstream and/or downstream of the first ion guide or the first collision, fragmentation or reaction device. The mass filter or mass analyser is preferably selected from the group consisting of: (i) a quadrupole rod set mass filter or analyser; (ii) a Time of Flight mass filter or mass analyser; (iii) a Wein filter; and (iv) a magnetic sector mass filter or mass analyser.

According to another aspect of the present invention there is provided a mass spectrometer comprising:
a first mass filter or mass analyser;
an ion mobility spectrometer or separator, the ion mobility spectrometer or separator being arranged downstream of the first mass filter or mass analyser; and
a second mass filter or mass analyser arranged downstream of the ion mobility spectrometer or separator.

The first mass filter or mass analyser and/or the second mass filter or mass analyser is preferably selected from the group consisting of: (i) a quadrupole rod set mass filter or analyser; (ii) a Time of Flight mass filter or mass analyser; (iii) a Wein filter; and (iv) a magnetic sector mass filter or mass analyser.

The first mass filter or mass analyser and/or the second mass filter or mass analyser preferably comprises a plurality of electrodes or rods. In a first mode of operation substantially all of the electrodes or rods of the first mass filter or mass analyser and/or the second mass filter or mass analyser may be maintained at substantially the same DC potential or voltage. In the first mode of operation the first mass filter or mass analyser and/or the second mass filter or mass analyser is preferably operated in a substantially non-resolving or ion guiding mode of operation.

In a second mode of operation adjacent electrodes or rods of the first mass filter or mass analyser and/or the second mass filter or mass analyser are preferably maintained at substantially different DC potentials or voltages. In the second mode of operation a DC potential or voltage difference is maintained between adjacent electrodes or rods of the first mass filter or mass analyser and/or the second mass filter or mass analyser, wherein the DC potential or voltage difference is preferably selected from the group consisting of: (i) <1 V; (ii) 1-2 V; (iii) 2-3 V; (iv) 3-4 V; (v) 4-5 V; (vi) 5-6 V; (vii) 6-7 V; (viii) 7-8 V; (ix) 8-9 V; (x) 9-10 V; (xi) 10-20 V; (xii) 20-30 V; (xiii) 30-40 V; (xiv) 40-50 V; (xv) 50-60 V; (xvi) 60-70 V; (xvii) 70-80 V; (xviii) 80-90 V; (xix) 90-100 V; and (xx) >100 V. In the second mode of operation opposed electrodes or rods of the first mass filter or mass analyser and/or the second mass filter or mass analyser are preferably maintained at substantially the same DC potential or voltage. In a mode of operation the first mass filter or mass analyser and/or the second mass filter or mass analyser is preferably operated in a resolving or mass filtering mode of operation.

In a mode of operation the first mass filter or mass analyser and/or the second mass filter or mass analyser is preferably scanned.

In a mode of operation the first mass filter or mass analyser and/or the second mass filter or mass analyser is preferably scanned in synchronism with the ion mobility spectrometer or separator.

In a mode of operation the first mass filter or mass analyser is scanned in synchronism with the second mass filter or mass analyser.

According to an embodiment the mass spectrometer preferably further comprises a first ion guide or a first collision, fragmentation or reaction device, wherein the first ion guide or the first collision, fragmentation or reaction device is arranged upstream of the ion mobility spectrometer or separator and/or downstream of the first mass filter or mass analyser.

The first collision, fragmentation or reaction device is preferably arranged and adapted to fragment ions by Collision Induced Dissociation ("CID").

Alternatively, the first collision, fragmentation or reaction device is selected from the group consisting of: (i) a Surface Induced Dissociation ("SID") fragmentation device; (ii) an Electron Transfer Dissociation fragmentation device; (iii) an Electron Capture Dissociation fragmentation device; (iv) an Electron Collision or Impact Dissociation fragmentation device; (v) a Photo Induced Dissociation ("PID") fragmentation device; (vi) a Laser Induced Dissociation fragmentation device; (vii) an infrared radiation induced dissociation device; (viii) an ultraviolet radiation induced dissociation device; (ix) a nozzle-skimmer interface fragmentation device; (x) an in-source fragmentation device; (xi) an ion-source Collision Induced Dissociation fragmentation device; (xii) a thermal or temperature source fragmentation device; (xiii) an electric field induced fragmentation device; (xiv) a magnetic field induced fragmentation device; (xv) an enzyme digestion or enzyme degradation fragmentation device; (xvi) an ion-ion reaction fragmentation device; (xvii) an ion-molecule reaction fragmentation device; (xviii) an ion-atom reaction fragmentation device; (xix) an ion-metastable ion reaction fragmentation device; (xx) an ion-metastable molecule reaction fragmentation device; (xxi) an ion-metastable atom reaction fragmentation device; (xxii) an ion-ion reaction device for reacting ions to form adduct or product ions; (xxiii) an ion-molecule reaction device for reacting ions to form adduct or product ions; (xxiv) an ion-atom reaction device for reacting ions to form adduct or product ions; (xxv) an ion-metastable ion reaction device for reacting ions to form adduct or product ions; (xxvi) an ion-metastable molecule reaction device for reacting ions to form adduct or product ions; and (xxvii) an ion-metastable atom reaction device for reacting ions to form adduct or product ions.

The first ion guide or the first collision, fragmentation or reaction device preferably comprises:

(i) a multipole rod set or a segmented multipole rod set;
(ii) an ion tunnel or ion funnel; or
(iii) a stack or array of planar, plate or mesh electrodes.

The multipole rod set preferably comprises a quadrupole rod set, a hexapole rod set, an octapole rod set or a rod set comprising more than eight rods.

The ion tunnel or ion funnel preferably comprises a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger and/or smaller in size or in area. Preferably, at least 5%, 10%, 15%, 20%, 25%, 30%, 35%, 40%, 45%, 50%, 55%, 60%, 65%, 70%, 75%, 80%, 85%, 90%, 95% or 100% of the electrodes have internal diameters or dimensions selected from the group consisting of: (i) ≤1.0 mm; (ii) ≤2.0 mm; (iii) ≤3.0 mm; (iv) ≤4.0 mm; (v) ≤5.0 mm; (vi) ≤6.0 mm; (vii) ≤7.0 mm; (viii) ≤8.0 mm; (ix) ≤9.0 mm; (x) ≤10.0 mm; and (xi) >10.0 mm.

The stack or array of planar, plate or mesh electrodes preferably comprises a plurality or at least 2, 3, 4, 5, 6, 7, 8, 9, 10, 11, 12, 13, 14, 15, 16, 17, 18, 19 or 20 planar, plate or mesh electrodes arranged generally in the plane in which ions travel in use, wherein at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in the plane in which ions travel in use.

The mass spectrometer preferably further comprises AC or RF voltage means for supplying the plurality of planar, plate or mesh electrodes with an AC or RF voltage and wherein adjacent planar, plate or mesh electrodes are preferably supplied with opposite phases of the AC or RF voltage.

The first ion guide or the first collision, fragmentation or reaction device preferably comprises a plurality of axial segments or at least 5, 10, 15, 20, 25, 30, 35, 40, 45, 50, 55, 60, 65, 70, 75, 80, 85, 90, 95 or 100 axial segments.

According to an embodiment the mass spectrometer preferably further comprises transient DC voltage means arranged and adapted to apply one or more transient DC voltages or potentials or one or more transient DC voltage or potential waveforms to electrodes forming the first ion guide or the first collision, fragmentation or reaction device in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the first ion guide or the first collision, fragmentation or reaction device.

According to another embodiment the mass spectrometer preferably further comprises AC or RF voltage means arranged and adapted to apply two or more phase-shifted AC or RF voltages to electrodes forming the first ion guide or the first collision, fragmentation or reaction device in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the first ion guide or the first collision, fragmentation or reaction device.

According to an embodiment the first ion guide or the first collision, fragmentation or reaction device has an axial length selected from the group consisting of: (i) <20 mm; (ii) 20-40 mm; (iii) 40-60 mm; (iv) 60-80 mm; (v) 80-100 mm; (vi) 100-120 mm; (vii) 120-140 mm; (viii) 140-160 mm; (ix) 160-180 mm; (x) 180-200 mm; (xi) 200-220 mm; (xii) 220-240 mm; (xiii) 240-260 mm; (xiv) 260-280 mm; (xv) 280-300 mm; and (xvi) >300 mm.

The first ion guide or the first collision, fragmentation or reaction device preferably further comprises AC or RF voltage means arranged and adapted to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of the plurality of electrodes of the first ion guide or the first collision, fragmentation or reaction device in order to confine ions radially within the first ion guide or the first collision, fragmentation or reaction device.

The AC or RF voltage means is preferably arranged and adapted to supply an AC or RF voltage to the plurality of electrodes of the first ion guide or the first collision, fragmentation or reaction device having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

According to an embodiment the AC or RF voltage means is preferably arranged and adapted to supply an AC or RF voltage to the plurality of electrodes of the first ion guide or the first collision, fragmentation or reaction device having a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5

MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

Preferably, singly charged ions having a mass to charge ratio in the range of 1-100, 100-200, 200-300, 300-400, 400-500, 500-600, 600-700, 700-800, 800-900 or 900-1000 have a drift or transit time through the first ion guide or the first collision, fragmentation or reaction device in the range: (i) 0-10 µs; (ii) 10-20 µs; (iii) 20-30 µs; (iv) 30-40 µs; (v) 40-50 µs; (vi) 50-60 µs; (vii) 60-70 µs; (viii) 70-80 µs; (ix) 80-90 µs; (x) 90-100 µs; (xi) 100-110 µs; (xii) 110-120 µs; (xiii) 120-130 µs; (xiv) 130-140 µs; (xv) 140-150 µs; (xvi) 150-160 µs; (xvii) 160-170 µs; (xviii) 170-180 µs; (xix) 180-190 µs; (xx) 190-200 µs; (xxi) 200-210 µs; (xxii) 210-220 µs; (xxiii) 220-230 µs; (xxiv) 230-240 µs; (xxv) 240-250 µs; (xxvi) 250-260 µs; (xxvii) 260-270 µs; (xxviii) 270-280 µs; (xxix) 280-290 µs; (xxx) 290-300 µs; and (xxxi) >300 µs.

According to an embodiment the mass spectrometer preferably further comprises means arranged and adapted to maintain at least a portion of the first ion guide or the first collision, fragmentation or reaction device at a pressure selected from the group consisting of: (i) >0.0001 mbar; (ii) >0.001 mbar; (iii) >0.01 mbar; (iv) >0.1 mbar; (v) >1 mbar; (vi) >10 mbar; (vii) 0.0001-0.1 mbar; and (viii) 0.001-0.01 mbar.

The mass spectrometer preferably further comprises first acceleration means arranged and adapted to accelerate ions into the first ion guide or the first collision, fragmentation or reaction device wherein in a mode of operation at least 5%, 10%, 15%, 20%, 25%, 30%, 35%, 40%, 45%, 50%, 55%, 60%, 65%, 70%, 75%, 80%, 85%, 90%, 95% or 100% of the ions are caused to fragment or react upon entering the first ion guide or the first collision, fragmentation or reaction device.

The mass spectrometer preferably further comprises a control system arranged and adapted to switch or repeatedly switch the potential difference through which ions pass prior to entering the first ion guide or the first collision, fragmentation or reaction device between a relatively high fragmentation or reaction mode of operation wherein ions are substantially fragmented or reacted upon entering the first ion guide or the first collision, fragmentation or reaction device and a relatively low fragmentation or reaction mode of operation wherein substantially fewer ions are fragmented or reacted or wherein substantially no ions are fragmented or reacted upon entering the first ion guide or the first collision, fragmentation or reaction device.

In the relatively high fragmentation or reaction mode of operation ions entering the first ion guide or the first collision, fragmentation or reaction device are preferably accelerated through a potential difference selected from the group consisting of: (i) ≥10 V; (ii) ≥20 V; (iii) ≥30 V; (iv) ≥40 V; (v) ≥50 V; (vi) ≥60 V; (vii) ≥70 V; (viii) ≥80 V; (ix) ≥90 V; (x) ≥100 V; (xi) ≥110 V; (xii) ≥120 V; (xiii) 130 V; (xiv) ≥140 V; (xv) ≥150 V; (xvi) ≥160 V; (xvii) ≥170 V; (xviii) ≥180 V; (xix) ≥190 V; and (xx) ≥200 V.

In the relatively low fragmentation or reaction mode of operation ions entering the first ion guide or the first collision, fragmentation or reaction device are preferably accelerated through a potential difference selected from the group consisting of: (i) ≤20 V; (ii) ≤15 V; (iii) ≤10 V; (iv) ≤5V; and (v) ≤1V.

The control system is preferably arranged and adapted to switch the first ion guide or the first collision, fragmentation or reaction device between the relatively high fragmentation or reaction mode of operation and the relatively low fragmentation or reaction mode of operation at least once every 1 ms, 5 ms, 10 ms, 15 ms, 20 ms, 25 ms, 30 ms, 35 ms, 40 ms, 45 ms, 50 ms, 55 ms, 60 ms, 65 ms, 70 ms, 75 ms, 80 ms, 85 ms, 90 ms, 95 ms, 100 ms, 200 ms, 300 ms, 400 ms, 500 ms, 600 ms, 700 ms, 800 ms, 900 ms, 1 s, 2 s, 3 s, 4 s, 5 s, 6 s, 7 s, 8 s, 9 s, or 10 s.

The first ion guide or the first collision, fragmentation or reaction device is preferably arranged and adapted to receive a beam of ions and to convert or partition the beam of ions such that at least 1, 2, 3, 4, 5, 6, 7, 8, 9, 10, 11, 12, 13, 14, 15, 16, 17, 18, 19 or 20 separate groups or packets of ions are confined and/or isolated in the first ion guide or the first collision, fragmentation or reaction device at any particular time. Each group or packet of ions is preferably separately confined and/or isolated in a separate axial potential well formed in the first ion guide or the first collision, fragmentation or reaction device.

The mass spectrometer preferably further comprises a second ion guide or a second collision, fragmentation or reaction device, wherein the second ion guide or the second collision, fragmentation or reaction device is arranged downstream of the ion mobility spectrometer or separator.

The second ion guide or the second collision, fragmentation or reaction device is preferably arranged and adapted to fragment ions by Collision Induced Dissociation ("CID").

Alternatively, the second ion guide or the second collision, fragmentation or reaction device may be selected from the group consisting of: (i) a Surface Induced Dissociation ("SID") fragmentation device; (ii) an Electron Transfer Dissociation fragmentation device; (iii) an Electron Capture Dissociation fragmentation device; (iv) an Electron Collision or Impact Dissociation fragmentation device; (v) a Photo Induced Dissociation ("PID") fragmentation device; (vi) a Laser Induced Dissociation fragmentation device; (vii) an infrared radiation induced dissociation device; (viii) an ultraviolet radiation induced dissociation device; (ix) a nozzle-skimmer interface fragmentation device; (x) an in-source fragmentation device; (xi) an ion-source Collision Induced Dissociation fragmentation device; (xii) a thermal or temperature source fragmentation device; (xiii) an electric field induced fragmentation device; (xiv) a magnetic field induced fragmentation device; (xv) an enzyme digestion or enzyme degradation fragmentation device; (xvi) an ion-ion reaction fragmentation device; (xvii) an ion-molecule reaction fragmentation device; (xviii) an ion-atom reaction fragmentation device; (xix) an ion-metastable ion reaction fragmentation device; (xx) an ion-metastable molecule reaction fragmentation device; (xxi) an ion-metastable atom reaction fragmentation device; (xxii) an ion-ion reaction device for reacting ions to form adduct or product ions; (xxiii) an ion-molecule reaction device for reacting ions to form adduct or product ions; (xxiv) an ion-atom reaction device for reacting ions to form adduct or product ions; (xxv) an ion-metastable ion reaction device for reacting ions to form adduct or product ions; (xxvi) an ion-metastable molecule reaction device for reacting ions to form adduct or product ions; and (xxvii) an ion-metastable atom reaction device for reacting ions to form adduct or product ions.

The second ion guide or the second collision, fragmentation or reaction device preferably comprises:
 (i) a multipole rod set or a segmented multipole rod set;
 (ii) an ion tunnel or ion funnel; or
 (iii) a stack or array of planar, plate or mesh electrodes.

The multipole rod set preferably comprises a quadrupole rod set, a hexapole rod set, an octapole rod set or a rod set comprising more than eight rods.

The ion tunnel or ion funnel preferably comprises a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger and/or smaller in size or in area. Preferably, at least 5%, 10%, 15%, 20%, 25%, 30%, 35%, 40%, 45%, 50%, 55%, 60%, 65%, 70%, 75%, 80%, 85%, 90%, 95% or 100% of the electrodes have internal diameters or dimensions selected from the group consisting of: (i) ≤1.0 mm; (ii) ≤2.0 mm; (iii) ≤3.0 mm; (iv) ≤4.0 mm; (v) ≤5.0 mm; (vi) ≤6.0 mm; (vii) ≤7.0 mm; ≤8.0 mm; (ix) ≤9.0 mm; (x) ≤10.0 mm; and (xi) >10.0 mm.

The stack or array of planar, plate or mesh electrodes preferably comprises a plurality or at least 2, 3, 4, 5, 6, 7, 8, 9, 10, 11, 12, 13, 14, 15, 16, 17, 18, 19 or 20 planar, plate or mesh electrodes arranged generally in the plane in which ions travel in use, wherein at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in the plane in which ions travel in use.

The mass spectrometer preferably further comprises AC or RF voltage means for supplying the plurality of planar, plate or mesh electrodes with an AC or RF voltage and wherein adjacent planar, plate or mesh electrodes are supplied with opposite phases of the AC or RF voltage.

The second ion guide or the second collision, fragmentation or reaction device preferably comprises a plurality of axial segments or at least 5, 10, 15, 20, 25, 30, 35, 40, 45, 50, 55, 60, 65, 70, 75, 80, 85, 90, 95 or 100 axial segments.

According to an embodiment the mass spectrometer preferably further comprises transient DC voltage means arranged and adapted to apply one or more transient DC voltages or potentials or one or more transient DC voltage or potential waveforms to electrodes forming the second ion guide or the second collision, fragmentation or reaction device in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the second ion guide or the second collision, fragmentation or reaction device.

According to another embodiment the mass spectrometer further comprises AC or RF voltage means arranged and adapted to apply two or more phase-shifted AC or RF voltages to electrodes forming the second ion guide or the second collision, fragmentation or reaction device in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the second ion guide or the second collision, fragmentation or reaction device.

The second ion guide or the second collision, fragmentation or reaction device preferably has an axial length selected from the group consisting of: (i) <20 mm; (ii) 20-40 mm; (iii) 40-60 mm; (iv) 60-80 mm; (v) 80-100 mm; (vi) 100-120 mm; (vii) 120-140 mm; (viii) 140-160 mm; (ix) 160-180 mm; (x) 180-200 mm; (xi) 200-220 mm; (xii) 220-240 mm; (xiii) 240-260 mm; (xiv) 260-280 mm; (xv) 280-300 mm; and (xvi) >300 mm.

The second ion guide or the second collision, fragmentation or reaction device preferably further comprises AC or RF voltage means arranged and adapted to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of the plurality of electrodes of the second ion guide or the second collision, fragmentation or reaction device in order to confine ions radially within the second ion guide or the second collision, fragmentation or reaction device.

The AC or RF voltage means is preferably arranged and adapted to supply an AC or RF voltage to the plurality of electrodes of the second ion guide or the second collision, fragmentation or reaction device having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage means is preferably arranged and adapted to supply an AC or RF voltage to the plurality of electrodes of the second ion guide or the second collision, fragmentation or reaction device having a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

According to an embodiment singly charged ions having a mass to charge ratio in the range of 1-100, 100-200, 200-300, 300-400, 400-500, 500-600, 600-700, 700-800, 800-900 or 900-1000 preferably have a drift or transit time through the second ion guide or the second collision, fragmentation or reaction device in the range: (i) 0-10 μs; (ii) 10-20 μs; (iii) 20-30 μs; (iv) 30-40 μs; (v) 40-50 μs; (vi) 50-60 μs; (vii) 60-70 μs; (viii) 70-80 μs; (ix) 80-90 μs; (x) 90-100 μs; (xi) 100-110 μs; (xii) 110-120 μs; (xiii) 120-130 μs; (xiv) 130-140 μs; (xv) 140-150 μs; (xvi) 150-160 μs; (xvii) 160-170 μs; (xviii) 170-180 μs; (xix) 180-190 μs; (xx) 190-200 μs; (xxi) 200-210 μs; (xxii) 210-220 μs; (xxiii) 220-230 μs; (xxiv) 230-240 μs; (xxv) 240-250 μs; (xxvi) 250-260 μs; (xxvii) 260-270 μs; (xxviii) 270-280 μs; (xxix) 280-290 μs; (xxx) 290-300 μs; and (xxxi) >300 μs.

The mass spectrometer preferably further comprises means arranged and adapted to maintain at least a portion of the second ion guide or the second collision, fragmentation or reaction device at a pressure selected from the group consisting of: (i) >0.0001 mbar; (ii) >0.001 mbar; (iii) >0.01 mbar; (iv) >0.1 mbar; (v) >1 mbar; (vi) >10 mbar; (vii) 0.0001-0.1 mbar; and (viii) 0.001-0.01 mbar.

The mass spectrometer preferably further comprises acceleration means arranged and adapted to accelerate ions emerging from the ion mobility spectrometer or separator into the second ion guide or the second collision, fragmentation or reaction device and wherein in a mode of operation at least 5%, 10%, 15%, 20%, 25%, 30%, 35%, 40%, 45%, 50%, 55%, 60%, 65%, 70%, 75%, 80%, 85%, 90%, 95% or 100% of the ions are caused to fragment or react upon entering the second ion guide or the second collision, fragmentation or reaction device.

The acceleration means is preferably arranged and adapted to progressively vary or increase the kinetic energy of ions emerging from the ion mobility spectrometer or separator as they are transmitted to the second ion guide or the second collision, fragmentation or reaction device.

The acceleration means preferably comprises a region across which a potential difference is maintained and wherein the potential difference is progressively varied or increased with time.

The mass spectrometer preferably further comprises a control system arranged and adapted to switch or repeatedly switch the potential difference through which ions pass prior to entering the second ion guide or the second collision, fragmentation or reaction device between a relatively high fragmentation or reaction mode of operation wherein ions are substantially fragmented or reacted upon entering the second ion guide or the second collision, fragmentation or reaction device and a relatively low fragmentation or reaction mode of operation wherein substantially fewer ions are fragmented or reacted or wherein substantially no ions are fragmented or reacted upon entering the second ion guide or the second collision, fragmentation or reaction device.

In the relatively high fragmentation or reaction mode of operation ions entering the second ion guide or the second collision, fragmentation or reaction device are preferably accelerated through a potential difference selected from the group consisting of: (i) ≥10 V; (ii) ≥20 V; (iii) ≥30 V; (iv) ≥40 V; (v) ≥50 V; (vi) ≥60 V; (vii) ≥70 V; (viii) ≥80 V; (ix) ≥90 V; (x) ≥100 V; (xi) ≥110 V; (xii) ≥120 V; (xiii) 130 V; (xiv) ≥140 V; (xv) ≥150 V; (xvi) ≥160 V; (xvii) ≥170 V; (xviii) ≥180 V; (xix) ≥190 V; and (xx) ≥200 V.

In the relatively low fragmentation or reaction mode of operation ions entering the second ion guide or the second collision, fragmentation or reaction device are preferably accelerated through a potential difference selected from the group consisting of: (i) ≤20 V; (ii) ≤15 V; (iii) ≤10 V; (iv) ≤5V; and (v) ≤1V.

The control system is preferably arranged and adapted to switch the second ion guide or the second collision, fragmentation or reaction device between the relatively high fragmentation or reaction mode of operation and the relatively low fragmentation or reaction mode of operation at least once every 1 ms, 5 ms, 10 ms, 15 ms, 20 ms, 25 ms, 30 ms, 35 ms, 40 ms, 45 ms, 50 ms, 55 ms, 60 ms, 65 ms, 70 ms, 75 ms, 80 ms, 85 ms, 90 ms, 95 ms, 100 ms, 200 ms, 300 ms, 400 ms, 500 ms, 600 ms, 700 ms, 800 ms, 900 ms, 1 ms, 2 ms, 3 ms, 4 ms, 5 ms, 6 ms, 7 ms, 8 s, 9 ms or 10 ms.

According to an embodiment the second ion guide or the second collision, fragmentation or reaction device is preferably arranged and adapted to receive a beam of ions from the ion mobility spectrometer or separator and to convert or partition the beam of ions such that at least 1, 2, 3, 4, 5, 6, 7, 8, 9, 10, 11, 12, 13, 14, 15, 16, 17, 18, 19 or 20 separate groups or packets of ions are confined and/or isolated in the second ion guide or the second collision, fragmentation or reaction device at any particular time. Each group or packet of ions is preferably separately confined and/or isolated in a separate axial potential well formed in the second ion guide or the second collision, fragmentation or reaction device.

The average ion mobility of ions in each of the groups or packets of ions confined and/or isolated in the second ion guide or the second collision, fragmentation or reaction device preferably progressively decreases with time and/or progressively decreases from the exit region of the second ion guide or the second collision, fragmentation or reaction device towards the entrance region of the second ion guide or the second collision, fragmentation or reaction device.

The second ion guide or the second collision, fragmentation or reaction device is preferably arranged and adapted to retain and/or confine and/or partition ions emerging from the ion mobility spectrometer or separator and to translate ions in one or more groups or packets of ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the second ion guide or the second collision, fragmentation or reaction device whilst either: (i) substantially maintaining the order and/or fidelity in which ions emerge from the ion mobility spectrometer or separator; and/or (ii) substantially maintaining the composition of ions as one or more groups or packets of ions are translated along the second ion guide or the second collision, fragmentation or reaction device.

The ion mobility spectrometer or separator preferably comprises a gas phase electrophoresis device.

According to an embodiment the ion mobility spectrometer or separator comprises:
(i) a drift tube;
(ii) a multipole rod set or a segmented multipole rod set;
(iii) an ion tunnel or ion funnel; or
(iv) a stack or array of planar, plate or mesh electrodes.

The drift tube preferably comprises one or more electrodes and means for maintaining an axial DC voltage gradient or a substantially constant or linear axial DC voltage gradient along at least 5%, 10%, 15%, 20%, 25%, 30%, 35%, 40%, 45%, 50%, 55%, 60%, 65%, 70%, 75%, 80%, 85%, 90%, 95% or 100% of the axial length of the drift tube.

The multipole rod set preferably comprises a quadrupole rod set, a hexapole rod set, an octapole rod set or a rod set comprising more than eight rods.

The ion tunnel or ion funnel preferably comprises a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger and/or smaller in size or in area. Preferably, at least 5%, 10%, 15%, 20%, 25%, 30%, 35%, 40%, 45%, 50%, 55%, 60%, 65%, 70%, 75%, 80%, 85%, 90%, 95% or 100% of the electrodes have internal diameters or dimensions selected from the group consisting of: (i) ≤1.0 mm; (ii) ≤2.0 mm; (iii) ≤3.0 mm; (iv) ≤4.0 mm; (v) ≤5.0 mm; (vi) ≤6.0 mm; (vii) ≤7.0 mm; (viii) ≤8.0 mm; (ix) ≤9.0 mm; (x) ≤10.0 mm; and (xi) >10.0 mm.

The stack or array of planar, plate or mesh electrodes preferably comprises a plurality or at least 2, 3, 4, 5, 6, 7, 8, 9, 10, 11, 12, 13, 14, 15, 16, 17, 18, 19 or 20 planar, plate or mesh electrodes wherein at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in the plane in which ions travel in use. Preferably, at least some or at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are supplied with an AC or RF voltage and wherein adjacent planar, plate or mesh electrodes are supplied with opposite phases of the AC or RF voltage.

The ion mobility spectrometer or separator preferably comprises a plurality of axial segments or at least 5, 10, 15, 20, 25, 30, 35, 40, 45, 50, 55, 60, 65, 70, 75, 80, 85, 90, 95 or 100 axial segments.

According to an embodiment the mass spectrometer preferably comprises DC voltage means for maintaining a substantially constant DC voltage gradient along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator in order to urge at least some ions along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator.

According to an embodiment the mass spectrometer further comprises transient DC voltage means arranged and adapted to apply one or more transient DC voltages or potentials or one or more transient DC voltage or potential waveforms to electrodes forming the ion mobility spectrometer or separator in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator.

According to an embodiment the mass spectrometer comprises AC or RF voltage means arranged and adapted to apply two or more phase-shifted AC or RF voltages to electrodes forming the ion mobility spectrometer or separator in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion mobility spectrometer or separator.

The ion mobility spectrometer or separator preferably has an axial length selected from the group consisting of: (i) <20 mm; (ii) 20-40 mm; (iii) 40-60 mm; (iv) 60-80 mm; (v) 80-100 mm; (vi) 100-120 mm; (vii) 120-140 mm; (viii) 140-160 mm; (ix) 160-180 mm; (x) 180-200 mm; (xi) 200-220 mm; (xii) 220-240 mm; (xiii) 240-260 mm; (xiv) 260-280 mm; (xv) 280-300 mm; and (xvi) >300 mm.

The ion mobility spectrometer or separator preferably further comprises AC or RF voltage means arranged and adapted to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of the plurality of electrodes of the ion mobility spectrometer or separator in order to confine ions radially within the ion mobility spectrometer or separator.

The AC or RF voltage means is preferably arranged and adapted to supply an AC or RF voltage to the plurality of electrodes of the ion mobility spectrometer or separator having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage means is preferably arranged and adapted to supply an AC or RF voltage to the plurality of electrodes of the ion mobility spectrometer or separator having a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

According to an embodiment singly charged ions having a mass to charge ratio in the range of 1-100, 100-200, 200-300, 300-400, 400-500, 500-600, 600-700, 700-800, 800-900 or 900-1000 have a drift or transit time through the ion mobility spectrometer or separator in the range: (i) 0-1 ms; (ii) 1-2 ms; (iii) 2-3 ms; (iv) 3-4 ms; (v) 4-5 ms; (vi) 5-6 ms; (vii) 6-7 ms; (viii) 7-8 ms; (ix) 8-9 ms; (x) 9-10 ms; (xi) 10-11 ms; (xii) 11-12 ms; (xiii) 12-13 ms; (xiv) 13-14 ms; (xv) 14-15 ms; (xvi) 15-16 ms; (xvii) 16-17 ms; (xviii) 17-18 ms; (xix) 18-19 ms; (xx) 19-20 ms; (xxi) 20-21 ms; (xxii) 21-22 ms; (xxiii) 22-23 ms; (xxiv) 23-24 ms; (xxv) 24-25 ms; (xxvi) 25-26 ms; (xxvii) 26-27 ms; (xxviii) 27-28 ms; (xxix) 28-29 ms; (xxx) 29-30 ms; (xxxi) 30-35 ms; (xxxii) 35-40 ms; (xxxiii) 40-45 ms; (xxxiv) 45-50 ms; (xxxv) 50-55 ms; (xxxvi) 55-60 ms; (xxxvii) 60-65 ms; (xxxviii) 65-70 ms; (xxxix) 70-75 ms; (xl) 75-80 ms; (xli) 80-85 ms; (xlii) 85-90 ms; (xliii) 90-95 ms; (xliv) 95-100 ms; and (xlv) >100 ms.

According to an embodiment the mass spectrometer further comprises means arranged and adapted to maintain at least a portion of the ion mobility spectrometer or separator at a pressure selected from the group consisting of: (i) >0.001 mbar; (ii) >0.01 mbar; (iii) >0.1 mbar; (iv) >1 mbar; (v) >10 mbar; (vi) >100 mbar; (vii) 0.001-100 mbar; (viii) 0.01-10 mbar; and (ix) 0.1-1 mbar.

The mass spectrometer further comprises means for introducing a first gas into the ion mobility spectrometer or separator, the first gas being selected from or at least partially comprising a gas selected from the group consisting of: (i) nitrogen; (ii) argon; (iii) helium; (iv) methane; (v) neon; (vi) xenon; and (vii) air.

The mass spectrometer preferably further comprises a housing for the ion mobility spectrometer or separator, the housing forming a substantially gas tight enclosure apart from an ion entrance aperture, an ion exit aperture and a port for introducing a gas into the housing.

The mass spectrometer preferably further comprises means for pulsing ions into the ion mobility spectrometer or separator once every 0-5 ms, 5-10 ms, 10-15 ms, 15-20 ms, 20-25 ms, 25-30 ms, 30-35 ms, 35-40 ms, 40-45 ms, 45-50 ms, 50-55 ms, 55-60 ms, 60-65 ms, 65-70 ms, 70-75 ms, 75-80 ms, 80-85 ms, 85-90 ms, 90-95 ms, 95-100 ms or >100 ms.

The mass spectrometer preferably further comprises an ion source. The ion source is preferably selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation On Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; and (xviii) a Thermospray ion source.

The ion source may comprise a pulsed or continuous ion source.

The mass spectrometer may further comprise a mass analyser. The mass analyser may be selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) an axial acceleration Time of Flight mass analyser.

The mass spectrometer preferably further comprises an ion detector.

According to another aspect of the present invention there is provided a method of mass spectrometry comprising:

fragmenting or reacting ions in a first ion guide or a first collision, fragmentation or reaction device to produce product, daughter, adduct or fragment ions; and temporally separating product, daughter, adduct or fragment ions according to their ion mobility which emerge from or which have been transmitted from the first ion guide or the first collision, fragmentation or reaction device in an ion mobility spectrometer or separator.

According to another aspect of the present invention there is provided a method of mass spectrometry comprising:

mass filtering of mass analysing ions in a first mass filter or mass analyser;

temporally separating ions in an ion mobility spectrometer or separator, the ion mobility spectrometer or separator being arranged downstream of the first mass filter or mass analyser; and mass filtering or mass analysing ions in a second mass filter or mass analyser arranged downstream of the ion mobility spectrometer or separator.

Ions in the ion mobility spectrometer or separator are preferably subjected to an electric field in the presence of a buffer gas. Different species preferably acquire different velocities and are preferably separated according to their ion mobility or another physico-chemical property. The mobility of an ion in such a spectrometer depends on its size, shape and charge.

In a preferred embodiment ions having one or more specific mass to charge ratios are first transmitted through a mass filter. The ions are then fragmented or reacted in a collision, fragmentation or reaction device. The resulting fragment, daughter, product or adduct ions are then preferably temporally separated in an ion mobility spectrometer or separator and detected. The mass filter preferably comprises a quadrupole mass filter although other types of mass filter are also contemplated.

According to a preferred embodiment a method of mass spectrometry is provided comprising fragmenting or reacting ions, providing a pulse of fragment, daughter, product or adduct ions and temporally separating at least some of the ions according to their ion mobility in an ion mobility spectrometer or separator before providing another pulse of ions, and detecting some of the fragment, daughter, product or adduct ions.

The use of an ion mobility spectrometer or separator rather than a mass filter to analyse fragment or daughter ions has the advantage that several or all of the different fragment or daughter ions may be detected. This provides a means of detecting more ions than would be detected using a quadrupole rod set mass filter or mass analyser to transmit only ions having a narrow range of mass to charge ratios. It also provides a means of measuring the relative abundance of two or more specific fragment, daughter, product or adduct ions which in turn provides a means of confirming an analysis. Although a quadrupole rod set mass filter may be programmed to switch to transmit different fragment or daughter ions for the purpose of confirmation of the analysis, there is an inevitable corresponding reduction in the duty cycle for the measurement of each specific fragment ion. This leads to a loss in sensitivity for each specific fragment or daughter ion. In contrast the preferred embodiment comprising an ion mobility spectrometer or separator separates the different fragment, daughter, product or adduct ions in time such that each species of ion can be recorded without any loss in duty cycle or sensitivity.

According to an embodiment of the present invention ions having one or more specific mass to charge ratios are transmitted through a first mass filter before being fragmented or reacted in a collision, fragmentation or reaction device. The resulting fragment, daughter, adduct or product ions are then preferably temporally separated in an ion mobility spectrometer or separator. Fragment, daughter, adduct or product ions having one or more specific mass to charge ratios are then preferably transmitted through a second mass filter and the ions are detected by an ion detector. The first and second mass filters preferably comprise quadrupole mass filters, although other types of mass filter are also contemplated.

According to another embodiment ions having one or more specific mass to charge ratios are transmitted through a first mass filter before being fragmented or reacted in a first collision, fragmentation or reaction device. The resulting fragment, daughter, adduct or product ions are then preferably temporally separated in an ion mobility spectrometer or separator. The fragment, daughter, adduct or product ions are then preferably further fragmented in a second collision, fragmentation or reaction device and second generation fragment, daughter, product or adduct ions having one or more specific mass to charge ratios are preferably transmitted through a second mass filter and are preferably detected by an ion detector. The first and second mass filters preferably comprise quadrupole mass filters, although other types of mass filter are also contemplated.

As in a triple quadrupole mass spectrometer, the specificity of the analysis may be improved by removing any parent or precursor ions which may be present prior to fragmentation or reaction in the collision, fragmentation or reaction device. Ions may be arranged to pass through a mass filter positioned upstream of the collision, fragmentation or reaction device. The mass filter preferably comprises a quadrupole rod set mass filter, although other types of mass filter are also contemplated. The mass filter may be set so as to transmit all ions or it may be set so as to transmit just selected parent or precursor ions of interest.

Although the ion mobility spectrometer or separator according to the preferred embodiment is preferably arranged so as to transmit substantially all ions, it may not have as high a specificity as a quadrupole rod set mass filter. The effective resolution of an ion mobility spectrometer or separator may be typically around 20 whereas the resolution of a quadrupole rod set mass filter may be unit mass i.e. a quadrupole rod set mass filter may have a resolution of 100 at mass to charge ratio 100, or a resolution of 200 at mass to charge ratio 200, or a resolution of 500 at mass to charge ratio 500 and so on.

In view of the lower resolution of the ion mobility spectrometer or separator, according to a particularly preferred embodiment ions which are onwardly transmitted from the ion mobility spectrometer or separator are preferably passed through a mass filter which is preferably positioned or arranged downstream of the ion mobility spectrometer or separator. The mass filter is preferably located upstream of the ion detector.

The mass filter arranged downstream of ion mobility spectrometer or separator preferably comprises a quadrupole rod set mass filter, although other types of mass filter are also contemplated. The mass filter may be set so as to transmit all ions or it may be set so as to transmit just ions of interest. When set to transmit all ions then the ion mobility spectrometer or separator may be used exclusively to analyse fragment, daughter, product or adduct ions. However, the mass filter may be set so as to transmit a number of specific fragment, daughter, product or adduct ions.

In a preferred embodiment the mass filter arranged downstream of the ion mobility spectrometer or separator may be set so as to switch to a number of pre-selected mass to charge ratios at pre-selected times during the course of the ion mobility separation cycle time. The pre-selected mass to charge ratio transmission windows may be chosen so as to correspond to the mass to charge ratios of a number of specific fragment, daughter, product or adduct ions of interest. The pre-selected times may be set to encompass the predicted exit or elution times of these specifically selected fragment, daughter, product or adduct ions from the ion mobility spectrometer or separator. According to this embodiment a number of fragment, daughter, product or adduct ions may be measured with the specificity of the mass filter but without any loss in the duty cycle and therefore without any loss in sensitivity.

In another embodiment, the mass filter arranged downstream of the ion mobility spectrometer or separator may be scanned in synchronism with the ion mobility spectrometer or separator cycle time. The scan law or scan function of the mass filter may be arranged so as to match as closely as possible the relationship between the mass to charge ratio of an ion and its exit or elution time from the ion mobility spectrometer or separator such that a substantial number of ions (either parent or precursor ions or fragment, daughter, product or adduct ions) exiting the ion mobility spectrometer or separator are subsequently transmitted through the mass filter.

The maximum scan rate for a typical quadrupole mass filter is typically of the order of 10 to 20 Daltons per ms whilst the experiment run time for a typical ion mobility spectrometer or separator may typically be of the order of 5 to 20 ms. It is apparent that for some applications a conventional quadrupole mass filter may not be able to be scanned fast enough in order to keep up with the arrival rate of ions at the exit the ion mobility spectrometer or separator. According to an embodiment the quadrupole mass filter arranged downstream of the ion mobility spectrometer or separator may be arranged to have a faster scan rate by, for example, reducing the length of the rod set. The ion mobility spectrometer or separator may also be arranged to have a longer drift time by, for example, increasing the length of the ion mobility spectrometer or separator.

According to an embodiment of the present invention there is provided a mass spectrometer comprising an ion source, a first mass filter, a collision, fragmentation or reaction device and a means for releasing a packet of fragment, daughter, product or adduct ions in a pulse to the collision, fragmentation or reaction device. The mass spectrometer preferably further comprises an ion mobility spectrometer or separator, a second mass filter and an ion detector. A second fragmentation, collision or reaction device may be arranged downstream of the ion mobility spectrometer or separator and upstream of the second mass filter.

The second collision, fragmentation or reaction device preferably allows fragment, daughter, product or adduct ions which emerge from the ion mobility spectrometer or separator to be further fragmented or reacted so as to form second generation fragment, daughter, product or adduct ions (i.e. grand-daughter ions). The grand-daughter ions may then be subsequently analysed by the second mass filter.

Each fragment, daughter, product or adduct ion as it exits the ion mobility spectrometer or separator may be fragmented or reacted so as to form a plurality of second generation or grand-daughter ions. One or more specific grand-daughter ions may be arranged so as to be transmitted through the second mass filter and hence subsequently be detected by the ion detector. The detection of a specific grand-daughter ion from a specific daughter, fragment, product or adduct ion (itself derived from a specific parent or precursor ion) provides even greater specificity. Furthermore, several combinations of daughter, fragment, product or adduct ions and grand-daughter ions from a single parent or precursor ion may be detected without any reduction in the duty cycle for the measurement of each grand-daughter ion. Therefore, several combinations of daughter, fragment, product or adduct ions and grand-daughter ions from a single parent or precursor ion may be detected without any loss of sensitivity.

According to an embodiment there is provided a means for receiving and fragmenting or reacting ions, a means for storing fragment, daughter, product or adduct ions, means for releasing a pulse of ions to an ion mobility spectrometer or separator and a means for detecting ions.

Ions may be received by and fragmented or reacted in a collision cell or other collision, fragmentation or reaction device. The collision cell or other collision, fragmentation or reaction device may be maintained at a pressure between $10^{-4}$ mbar and 1 mbar, or more preferably between $10^{-3}$ and $10^{-1}$ mbar. The collision cell or other collision, fragmentation or reaction device may comprise an AC or RF ion guide wherein ions are confined close to the central axis even when undergoing collisions with background gas molecules. The RF ion guide may comprise a multipole rod set ion guide wherein an AC or RF voltage is applied between neighbouring rods, or a ring stack wherein an AC or RF voltage is applied between neighbouring rings, or one of many other types of RF ion guide. Ions entering the collision cell with an energy at least 10 eV or greater may undergo multiple collisions with gas molecules and may be induced to fragment.

The collision, fragmentation or reaction device may also be used to store ions and release ions in pulses. A plate or electrode at the exit of the collision, fragmentation or reaction device may be set to a voltage such as to form a potential barrier thereby preventing ions from exiting the collision, fragmentation or reaction device. For positive ions, a potential of about +10V with respect to the collision, fragmentation or reaction device may be adequate. A similar plate or electrode at a similar potential at the entrance to the collision, fragmentation or reaction device may also prevent ions from leaving or exiting the collision, fragmentation or reaction device via the entrance. If the potential on the plate or electrode at the exit of the collision, fragmentation or reaction device is momentarily lowered to 0 V or less than 0 V with respect to the collision, fragmentation or reaction device then ions will be preferably released in a pulse. The release of a pulse of ions into the ion mobility spectrometer or separator preferably marks the start of a new ion mobility separation experiment.

Ions in the preferred ion mobility spectrometer or separator are preferably subjected to an electric field in the presence of a buffer gas. Different species of ion preferably acquire different velocities and preferably become separated according to their ion mobility or another physico-chemical property. The mobility of an ion in such an ion mobility spectrometer or separator preferably depends upon its size, shape and charge. One form of an ion mobility spectrometer or separator consists of a drift tube or cell in which an axial electric field is maintained. The presence of a buffer gas causes ions having a relatively high ion mobility to pass more quickly through the device than ions having a relatively low ion mobility. As a result ions are caused to separate according to their ion mobility. The drift cell may also act as an ion guide in that ions may be radially confined within the drift cell by the application of an inhomogeneous AC or RF field to the electrodes comprising the drift cell.

The ion mobility spectrometer or separator may be arranged so as to radially confine ions by applying an inhomogeneous AC or RF field to the ion guide such that ions are propelled forward by a potential hill or barrier that preferably moves along the axis of the ion guide in the presence of a buffer gas. Appropriate selection of the amplitude and velocity of the travelling potential barrier and the type and pressure of gas preferably allows ions to selectively slip according to their ion mobility. This in turn allows ions of different ion mobility to be transported at different velocities and thereby separated.

The cycle time for an ion mobility separation experiment may be between 2 and 50 ms, more preferably between 5 and 20 ms, and yet more preferably about 10 ms. Ions exiting the ion mobility spectrometer or separator are preferably detected and recorded. The cycle may then be repeated.

An ion source may be provided which preferably comprises a pulsed ion source such as a Laser Desorption Ionisation ion source, a Matrix Assisted Laser Desorption/Ionisation ion source or a Desorption/Ionisation on Silicon ion sources.

Alternatively, a continuous ion source may be used. The continuous ion source may comprise an Electrospray Ionisation ion source, an Atmospheric Pressure Chemical Ionisation ion source, an Electron Impact ion source, an Atmospheric Pressure Photon Ionisation ion source, a Chemical Ionisation ion source, a Fast Atom Bombardment ion source, a Liquid Secondary Ion Mass Spectrometry ion source, a Field Ionisation ion source, a Field Desorption ion sources. Other continuous or pseudo-continuous ion sources may also be used.

The mass spectrometer may comprise a mass filter arranged downstream of the ion source and upstream of the collision, fragmentation or reaction device. The mass filter may be used to transmit ions having a single specific mass to charge ratio or ions having a range of mass to charge ratios. The mass filter may comprise a multipole rod set mass filter, a quadrupole mass filter, a Time of Flight mass filter, a Wein filter or a magnetic sector mass filter or mass analyser.

The mass spectrometer may comprise a second mass filter preferably arranged downstream of the ion mobility spectrometer or separator and preferably upstream of the ion detector. The second mass filter may be arranged to transmit ions having a single specific mass to charge ratio or ions having a range of mass to charge ratios. The second mass filter may comprise a multipole rod set mass filter, a quadrupole mass filter, a Time of Flight mass filter, a Wein filter, or a magnetic sector mass filter or mass analyser.

The mass spectrometer may also comprise a second collision, fragmentation or reaction device arranged downstream of the ion mobility spectrometer or separator and preferably upstream of the second mass filter. In one mode of operation at least some ions entering the second collision, fragmentation or reaction device are preferably caused to fragment or reset.

The second collision, fragmentation or reaction cell may be maintained at a pressure between $10^{-4}$ mbar and 1 mbar, or more preferably between $10^{-3}$ and $10^{-1}$ mbar. The second collision, fragmentation or reaction device may include an AC or RF ion guide to confine the ions close to the central axis even when undergoing collisions with background gas molecules. The AC or RF ion guide may comprise a multipole rod set ion guide wherein an AC or RF voltage is applied between neighbouring rods, or a ring stack with RF voltage applied between neighbouring rings, or one of many other types of AC or RF ion guide. Ions entering the second collision, fragmentation or reaction device with an energy at least 10 eV or greater may preferably undergo multiple collisions with gas molecules and may be induced to fragment.

BRIEF DESCRIPTION OF THE DRAWINGS

Various embodiments of the present invention will now be described, by way of example only, and with reference to the accompanying drawings in which.

DETAILED DESCRIPTION OF THE PREFERRED EMBODIMENTS

Figure 1:
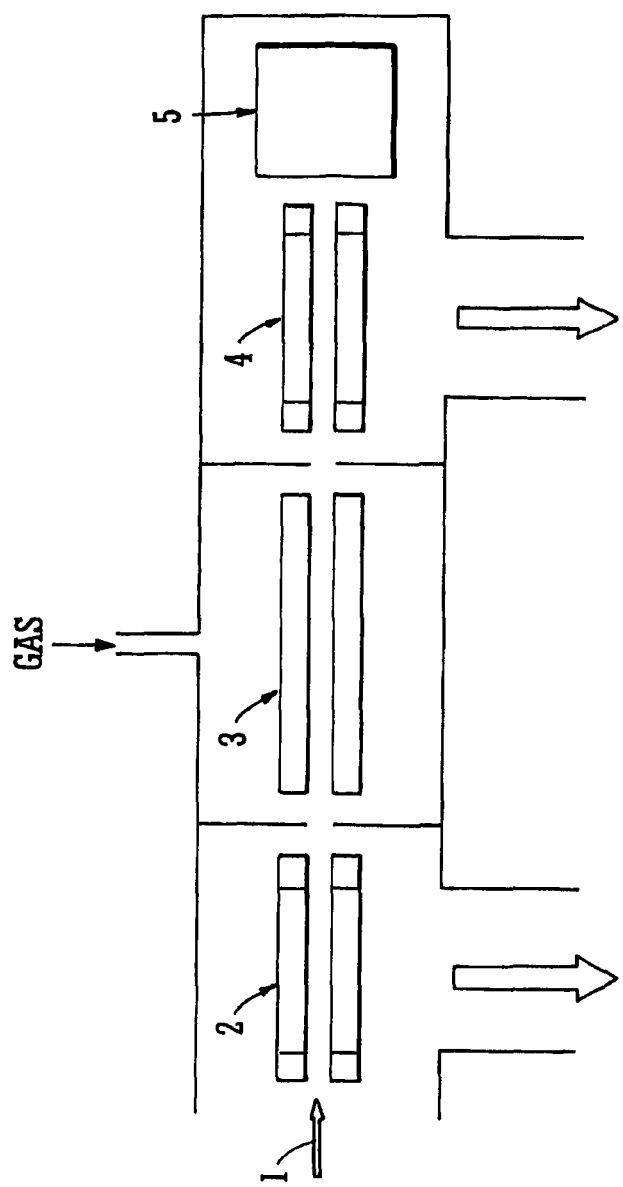
FIG. 1 shows a conventional triple quadrupole mass spectrometer.

A conventional triple quadrupole mass spectrometer is shown in FIG. 1. Ions 1 from an ion source (not shown) are passed to a quadrupole rod set mass filter 2. The quadrupole rod set mass filter 2 is arranged to selectively transmit parent or precursor ions having a specific mass to charge ratio. The selected parent or precursor ions are then onwardly transmitted and accelerated into a collision cell 3 comprising a relatively high pressure quadrupole rod set ion guide supplied with a collision gas.

The selected parent or precursor ions which enter the collision cell 3 undergo multiple collisions with collision gas molecules present in the collision cell 3. The parent or precursor ions are induced to fragment forming fragment or daughter ions in the process. The resulting fragment or daughter ions and any unfragmented precursor or parent ions are then passed from the collision cell 3 to a quadrupole rod set mass analyser 4 which is arranged downstream of the collision cell 3. The quadrupole rod set mass analyser 4 arranged downstream of the collision cell 3 may be scanned. Fragment or daughter ions transmitted by the quadrupole rod set mass analyser 4 are then detected by an ion detector 5 which is arranged downstream of the quadrupole rod set mass analyser 4.

The quadrupole rod set mass filter 2 arranged upstream of the collision cell 3 and the quadrupole mass analyser 4 arranged downstream of the collision cell 3 may be operated so as to transmit ions having a single or a specific mass to charge ratio. The quadrupole mass filter 2 upstream of the collision cell 3 and the quadrupole rod set mass analyser 4 arranged downstream of the collision cell 3 will have duty cycle of substantially 100% when they are operated so as to transmit ions having a single specific mass to charge ratio.

The triple quadrupole mass spectrometer may be used to perform Selected Reaction Monitoring (SRM) experiments wherein specific parent or precursor ions are transmitted by the quadrupole mass filter 2 and are then fragmented in the collision cell 3. The quadrupole mass analyser 4 arranged downstream of the collision cell 3 may be set to monitor for specific fragment or daughter ions. Such an arrangement is very specific and exceptionally sensitive.

Triple quadrupole mass spectrometers have found significant use in the field of drug discovery and development where they may be used in both SRM and also MRM (Multiple Reaction Monitoring) modes to quantify target compounds.

Figure 2:
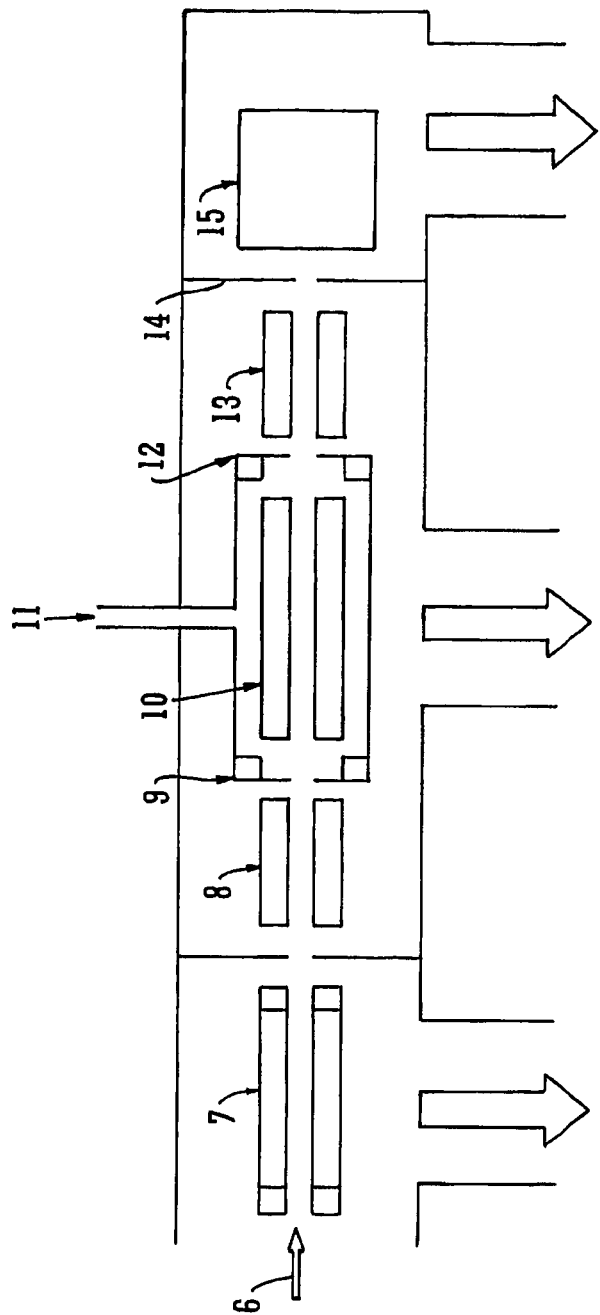
FIG. 2 shows a first embodiment of the present invention comprising a first mass filter, a collision, fragmentation or reaction device, an ion mobility spectrometer or separator, an ion guide and an ion detector.

FIG. 2 shows a mass spectrometer according to a first embodiment of the present invention. The mass spectrometer preferably comprises a quadrupole rod set mass filter 7, a collision, fragmentation or reaction device 8, an ion mobility spectrometer or separator 10, an ion guide 13 arranged downstream of the ion mobility spectrometer or separator 10 and an ion detector 15.

A continuous ion source (not shown) such as an Electrospray ion source may be provided. The ion source preferably generates a beam of ions 6 which are preferably passed to the quadrupole rod set mass filter 7 arranged upstream of the collision, fragmentation or reaction device 8.

Certain specific parent or precursor ions may be arranged so as to be selectively transmitted by the quadrupole rod set mass filter 7 and passed to the collision, fragmentation or reaction device 8 which is preferably arranged downstream of the quadrupole rod set mass filter 7.

In one embodiment the collision, fragmentation or reaction device 8 may also function as an ion trap. Parent or precursor ions may be arranged to enter the collision, fragmentation or reaction device 8 and according to an embodiment undergo multiple collisions with background gas molecules present in the collision, fragmentation or reaction device 8. The parent or precursor ions are preferably induced to react or fragment so as to form fragment, daughter, adduct or product ions. The resulting fragment, daughter, adduct or product ions and any remaining unfragmented parent or precursor ions are preferably trapped in the collision, fragmentation or reaction device 8.

Ions trapped within the collision, fragmentation or reaction device 8 may then preferably be pulsed out of the collision, fragmentation or reaction device 8 by, for example, the application of an extraction voltage to an ion gate 9 which is preferably located generally at the exit of the collision, fragmentation or reaction device 8. The ions which are pulsed or ejected out of the collision, fragmentation or reaction device 8 then preferably pass to an ion mobility spectrometer or separator 10 which is preferably arranged downstream of the collision, fragmentation or reaction device 8.

The collision, fragmentation or reaction device 8 may according to an embodiment comprise a quadrupole rod set or other multipole rod set preferably having a length of approximately 75 mm. According to another embodiment the collision, fragmentation or reaction device 8 may comprise an ion tunnel ion guide comprising a plurality of electrodes having apertures therein. The apertures of the electrodes are preferably all the same size. In other embodiments at least 60%, 65%, 70%, 75%, 80%, 85%, 90% or 95% of the electrodes of the collision, fragmentation or reaction device 8 have apertures which are substantially the same size. The collision, fragmentation or reaction device 8 may preferably comprise approximately 50 electrodes. Adjacent electrodes are preferably connected to opposite phases of a two-phase AC or RF voltage supply. The AC or RF voltage applied to the electrodes preferably causes a pseudo-potential well to be generated which preferably acts to radially confine ions within the collision, fragmentation or reaction device 8.

In the preferred embodiment the electrodes comprising the collision, fragmentation or reaction device 8 are preferably maintained at a DC voltage V1. The ion gate 9 downstream of the collision, fragmentation or reaction device 8 is preferably normally held at a DC voltage V2 which is preferably higher than V1. The voltage applied to the ion gate 9 may be periodically dropped or lowered to a voltage V3 which is preferably lower than V1. Ions may therefore be caused to be accelerated out of the ion collision, fragmentation or reaction device 8. The ions are then preferably admitted or pulsed into the ion mobility spectrometer or separator 10.

Adjacent electrodes which form the collision, fragmentation or reaction device 8 may be connected to opposite phases of an AC or RF voltage supply. The AC or RF voltage supply preferably has a frequency within the range 0.1-3.0 MHz, preferably 0.3-2.0 MHz, further preferably 0.5-1.5 MHz.

According to another embodiment, a pulsed ion source such as a Matrix Assisted Laser Desorption Ionisation ("MALDI") ion source or a Laser Desorption Ionisation ion source may be used instead of a continuous ion source. If a pulsed ion source is used then ion gate 9 may be omitted.

The ion mobility spectrometer or separator 10 preferably causes ions to become temporally separated according to their ion mobility. The ion mobility spectrometer or separator 10 may comprise a number of different forms.

In one embodiment the ion mobility spectrometer or separator 10 may comprise a drift tube comprising a number of guard rings distributed within the drift tube. The guard rings may be interconnected by equivalent valued resistors and may be connected to a DC voltage source. A linear DC voltage gradient may be generated which is preferably maintained along at least a portion of the length of the drift tube. The guard rings may not be connected to an AC or RF voltage source i.e. ions may not be radially confined within the ion mobility spectrometer or separator 10 according to this embodiment.

According to another embodiment the ion mobility spectrometer or separator 10 may comprise a number of ring, annular or plate electrodes. The electrodes preferably have an aperture therein through which ions are preferably transmitted. The apertures are preferably all the same size and are preferably circular. In other embodiments at least 60%, 65%, 70%, 75%, 80%, 85%, 90% or 95% of the electrodes have apertures which are substantially the same size or area. The ion mobility spectrometer or separator 10 may comprise a plurality of electrodes arranged in a vacuum chamber.

The ion mobility spectrometer or separator 10 preferably has a length of between 100 mm and 200 mm. The ion mobility spectrometer or separator 10 is preferably provided in a vacuum chamber which is preferably maintained, in use, at a pressure within the range 0.1-10 mbar. According to less preferred embodiments, the vacuum chamber may be maintained at a pressure greater than 10 mbar up to a pressure at or near atmospheric pressure. Also, according to less preferred embodiments, the vacuum chamber may alternatively be maintained at a pressure below 0.1 mbar.

Alternate electrodes of the ion mobility spectrometer or separator 10 are preferably coupled to opposite phases of a two-phase AC or RF voltage supply. The AC or RF voltage supply preferably has a frequency within the range 0.1-3.0 MHz, preferably 0.3-2.0 MHz, further preferably 0.5-1.5 MHz.

The electrodes comprising the collision, fragmentation or reaction device 8 and the electrodes comprising the ion mobility spectrometer or separator 10 may preferably be interconnected via resistors to a DC voltage supply which may comprise a 400 V supply. The resistors interconnecting electrodes forming the ion mobility spectrometer or separator 10 may be substantially equal in value in which case a linear axial DC voltage gradient may preferably be maintained along the length of the ion mobility spectrometer or separator 10. The DC voltage gradient may be linear or non-linear. According to an embodiment the DC voltage gradient is preferably stepped. The applied AC or RF voltage is preferably superimposed upon the DC voltage and serves to radially confine ions within the ion mobility spectrometer or separator 10. The DC voltages V2 or V3 applied to the ion gate 9 preferably float on the DC voltage supply. The AC or RF voltage supply is preferably isolated from the DC voltage supply by a capacitor.

In another embodiment the ion mobility spectrometer or separator 10 may comprise an ion guide comprising of a plurality of electrodes having apertures through which ions are transmitted in use. One or more transient DC voltages or potentials or one or more transient DC voltage or potential waveforms are preferably progressively applied to the electrodes. The apertures of the electrodes forming the ion mobility spectrometer or separator 10 are preferably all the same size. In other embodiments at least 60%, 65%, 70%, 75%, 80%, 85%, 90% or 95% of the electrodes have apertures which are substantially the same size. Adjacent electrodes are preferably connected to opposite phases of a two-phase AC or RF supply. One or more transient DC voltages or potentials or one or more transient DC voltage or potential waveforms are preferably applied to one or more electrodes of the ion mobility spectrometer or separator 10 in order to form one or more potential hills or barriers which are preferably translated along the length of the ion mobility spectrometer or separator 10. The one or more transient DC voltages or potentials or one or more transient DC voltage or potential waveforms are preferably progressively applied to a succession of electrodes forming the ion mobility spectrometer or separator such that the one or more potential hills or barriers move along the axis of the ion mobility spectrometer or separator 10 in the direction in which the ions are to be propelled or driven.

The ion mobility spectrometer or separator 10 is preferably provided in a vacuum chamber that is preferably maintained, in use, at a pressure within the range 0.1-10 mbar. According to a less preferred embodiment, the vacuum chamber may be maintained at a pressure greater than 10 mbar up to a pressure at or near atmospheric pressure. According to another less preferred embodiment the vacuum chamber may be maintained at a pressure below 0.1 mbar.

The presence of gas which the ion mobility spectrometer or separator 10 preferably imposes a viscous drag on the movement of ions and the amplitude and average velocity of the one or more potential hills or barriers is preferably set such that ions will, from time to time, slip over a potential hill or barrier. The lower the mobility of the ion the more likely the ion will be to slip or otherwise pass over a potential hill. This in turn allows ions having different ion mobilities to be transported at different velocities through the ion mobility spectrometer or separator 10 and therefore to become temporally separated.

Typical drift times through the preferred ion mobility spectrometer or separator 10 are of the order of a several milliseconds. After all the ions which have been pulsed into the ion mobility spectrometer or separator 10 have traversed the length of the ion mobility spectrometer or separator 10, a new pulse of ions is preferably admitted or pulsed into the ion nobility spectrometer or separator 10 which preferably marks the start of a new cycle of operation. Many cycles may be performed in a single experiment.

According to a preferred embodiment a differential pumping aperture 12 may preferably be provided downstream of the ion mobility spectrometer or separator 10. An ion guide 13 may also be provided downstream of the ion mobility spectrometer or separator 10. A further differential pumping aperture 14 may be provided downstream of the ion guide 13. A vacuum chamber housing an ion detector 15 may be arranged downstream of the further differential pumping aperture 14. The ion guide 13 may form an intermediate vacuum stage between that of the ion mobility spectrometer or separator 10 and that of the ion detector 15. According to an embodiment, the ion guide 13 may be maintained at substantially the same pressure as that of the collision, fragmentation or reaction device 8.

The ion guide 13 may comprise a quadrupole rod set or other multipole rod set and preferably has a length of approximately 75 mm. Alternatively, the ion guide 13 may comprise an ion tunnel ion guide comprising a plurality of electrodes having apertures therein. The apertures are preferably all the same size. In other embodiments at least 60%, 65%, 70%, 75%, 80%, 85%, 90% or 95% of the electrodes have apertures which are substantially the same size. The ion tunnel ion guide 13 may preferably comprise approximately 50 electrodes. Adjacent electrodes of the ion guide 13 are preferably connected to opposite phases of a two-phase AC or RF voltage supply so that ions are radially confined in use within the ion tunnel ion guide 13.

According to a particularly preferred embodiment the ion guide 13 may comprise an ion tunnel ion guide wherein one or more transient DC voltages or potentials or one or more transient DC voltage or potential waveforms are applied to the electrodes forming the ion guide 13. The apertures of the electrodes forming the ion guide 13 are preferably all the same size. In other embodiments at least 60%, 65%, 70%, 75%, 80%, 85%, 90% or 95% of the electrodes have apertures which are substantially the same size. Adjacent electrodes are preferably connected to opposite phases of a two-phase AC or RF supply.

The one or more transient DC voltages or one or more transient DC voltage waveforms applied to the electrodes of the ion guide 13 preferably form one or more potential hills or barriers. The one or more transient DC voltages or potentials or one or more transient DC voltage or potential waveforms are preferably progressively applied to a succession of electrodes of the ion guide 13 such that the one or more potential hills or barriers preferably move along the axis of the ion guide 13 towards the exit of the ion guide 13.

The ion guide 13 is preferably provided in a vacuum chamber which is preferably maintained, in use, at a pressure within the range $10^{-3}$ mbar to $10^{-1}$ mbar. According to a less preferred embodiment, the vacuum chamber may be maintained at a pressure greater than $10^{-3}$ mbar up to a pressure at or near 1 mbar. According to another less preferred embodiment the vacuum chamber may be maintained at a pressure below $10^{-3}$ mbar.

The gas pressure is preferably sufficient to impose collisional damping of ion motion, but is preferably not sufficient so as to impose excessive viscous drag on the movement of ions. The amplitude and average velocity of the one or more potential hills or barriers is preferably set such that ions will not slip over a potential hill or barrier. The ions are preferably transported ahead of each travelling potential hill or barrier regardless of their mass, or mass to charge ratio, or mobility.

The advantage of providing an ion guide 13 wherein one or more transient DC voltages or potentials or one or more transient DC voltage or potential waveforms are preferably applied to the electrodes forming the ion guide 13 is that the temporal separation of the ions exiting the ion mobility spectrometer or separator 10 may be maintained as the ions are transported by the ion guide 13 to the ion detector 15. The ion detector 15 is preferably able to record an ion mobility spectrum of fragment ions without any loss in resolution or specificity.

Figure 3:
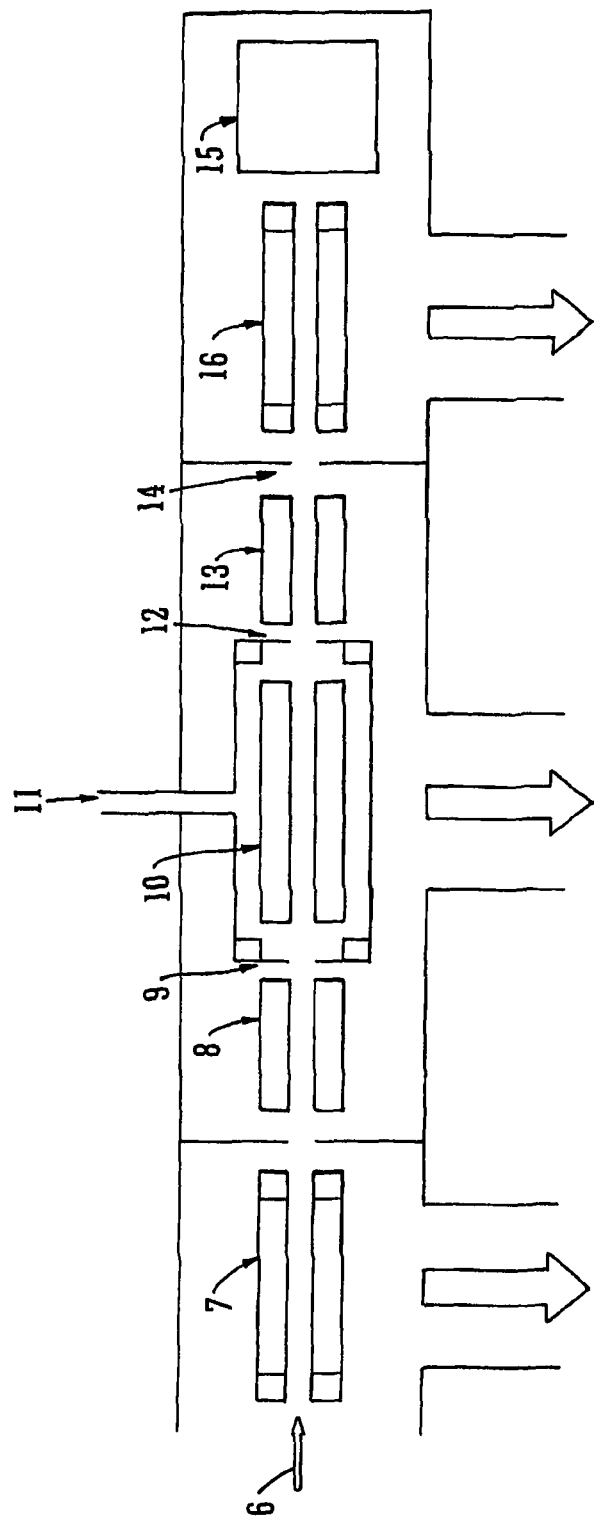
FIG. 3 shows a second embodiment of the present invention comprising a first mass filter, a collision, fragmentation or reaction device, an ion mobility spectrometer or separator, an ion guide, a second mass filter and an ion detector.

FIG. 3 shows a second embodiment of the present invention which is substantially similar in many respects to the first embodiment. According to this embodiment a second mass filter 16 is preferably additionally provided downstream of the ion guide 13 which is preferably arranged downstream of the ion mobility spectrometer or separator 10. The second mass filter 16 is preferably arranged upstream of the ion detector 15. As in the first embodiment illustrated in FIG. 2, a continuous ion source (e.g. an Electrospray ion source) preferably generates a beam of ions 6 which are then preferably passed to a first quadrupole rod set mass filter 7.

The ion sources and other aspects described in relation to the first main preferred embodiment may also be used or provided in relation to the second main preferred embodiment.

The first quadrupole rod set mass filter 7 is arranged to onwardly transmit certain specific parent or precursor ions which are then preferably arranged to enter a collision, fragmentation or reaction device 8 which is preferably arranged downstream of the first quadrupole rod set mass filter 7. The collision, fragmentation or reaction device 8 is preferably also arranged so as to trap ions. Ions in the collision, fragmentation or reaction device 8 may according to an embodiment undergo multiple collisions with background gas molecules and may be induced to fragment. Fragment, daughter, adduct or product ions and any remaining unfragmented parent or precursor ions are preferably trapped in the collision, fragmentation or reaction device 8. The ions are then preferably pulsed or ejected out of the collision, fragmentation or reaction device 8 by, for example, the application of an extraction voltage to an ion gate 9 which is preferably arranged at the exit of the collision, fragmentation or reaction device 8.

An ion mobility spectrometer or separator 10 is preferably arranged downstream of the collision, fragmentation or reaction device 8. The ion mobility spectrometer or separator 10 is preferably arranged to receive ions emitted from the collision, fragmentation, or reaction device 8.

The ion mobility spectrometer or separator 10 may comprise a drift tube having a number of guard rings distributed within the drift tube. In another embodiment alternate electrodes forming the ion mobility spectrometer or separator 10 may preferably be coupled to opposite phases of a two-phase AC or RF voltage supply. In another embodiment the ion mobility spectrometer or separator 10 may comprise a plurality of electrodes having apertures through which ions are transmitted in use. One or more transient DC voltages or potentials or one or more transient DC voltage or potential waveforms may be applied to the electrodes comprising the ion mobility spectrometer or separator 10.

A differential pumping aperture 12 may be provided downstream of the ion mobility spectrometer or separator 10. An ion guide 13 is preferably arranged downstream of the differential pumping aperture 12. A further differential pumping aperture 14 may be provided downstream of the ion guide 13. A second quadrupole rod set mass filter 16 is preferably provided downstream of the further differential pumping aperture 14. Ions transmitted by the second quadrupole mass filter 16 are preferably detected by an ion detector 15 which is preferably arranged downstream of the second quadrupole rod set mass filter 16.

The ion guide 13 arranged downstream of the ion mobility spectrometer or separator 10 preferably provides an intermediate vacuum stage between that of the ion mobility spectrometer or separator 10 and that of the second quadrupole rod set mass filter 16 and the ion detector 15. For convenience, the ion guide 13 may be maintained at the same pressure as that of the collision, fragmentation or reaction device 8 arranged upstream of the ion mobility spectrometer or separator 10.

The ion guide 13 arranged downstream of the ion mobility spectrometer or separator 10 may comprise a quadrupole rod set, or other multipole rod set. Alternatively, the ion guide 13 may, comprise an ion tunnel ion guide comprising a plurality of electrodes having apertures therein. One or more transient DC voltages or potentials or one or more voltage or potential waveforms may be applied to the electrodes of the ion guide 13. The gas pressure in the ion guide 13 may be sufficient so as to impose collisional damping of ion motion. The gas pressure is preferably not sufficient so as to impose excessive viscous drag on the movement of ions. Ions are preferably transported ahead of each travelling potential hill or barrier regardless of their mass, mass to charge ratio or ion mobility.

The advantage of using an ion guide 13 wherein one or more transient DC voltages or potentials or one or more transient DC voltage or potential waveforms are applied to the electrodes of the ion guide 13 is that the temporal separation of the ions exiting the ion mobility spectrometer or separator 10 can preferably be maintained as the ions are transported to or towards the second mass filter 16 and onwards to the ion detector 15.

The second mass filter 16 preferably comprises a quadrupole rod set mass filter. However, according to other less preferred embodiments the second mass filter 16 may comprise a different form of mass filter. The second mass filter 16 may be arranged so as to transmit all ions i.e. the second mass filter 16 may be operated in a non-resolving or ion guiding mode of operation. Alternatively, the second mass filter 16 may be arranged to transmit ions having a specific mass to charge ratio or having a range of mass to charge ratios.

In one mode of operation the second mass filter 16 may be set so as to transmit a single species of fragment, daughter, adduct or product ions during the course of an ion mobility separation cycle i.e. during the course of ions emerging from the ion mobility spectrometer or separator 10 and prior to a new pulse of ions being admitted into the ion mobility spectrometer or separator 10. The recording of a fragment, daughter, product or adduct ion with a specific mass to charge ratio and at a specific ion mobility elution time provides increased specificity of the measurement.

In another mode of operation the second mass filter 16 may be set so as to transmit a number of different specific fragment, daughter, product or adduct ions at a number of different specific ion mobility elution times. This provides the opportunity to measure more than one fragment, daughter, product or adduct ion without any loss in sensitivity for each fragment, daughter, product or adduct mass. Since more than one fragment, daughter, product or adduct ion may be measured, the total signal measured will be increased compared to the situation when just a single fragment, daughter, product or adduct mass is measured. The recording of a number of different fragment, daughter, product or adduct ions each having a specific mass to charge ratio and a specific ion mobility elution time provides an increased specificity for each measurement. The recording of several fragment, daughter, product or adduct ions, each with high specificity, allows the relative abundance of each fragment, daughter, product or adduct mass to be compared thereby providing a means of further validating the measurement.

In another mode of operation the second mass filter 16 may be scanned in order to transmit several or all of the different ions as they elute from the ion mobility spectrometer or separator 10. The scan law or scan function of the second mass filter 16 may be set so as to match as closely as possible the known elution time from the ion mobility spectrometer or separator 10 of ions having one or more specific charge states. This provides the opportunity to measure several or all of the parent, precursor or fragment, daughter, product or adduct ions with a high sampling duty cycle. This in turn provides a means of recording the complete parent or precursor or fragment, daughter, product or adduct ion mass spectrum using a quadrupole mass filter with increased sensitivity.

The transit time of ions through a conventional quadrupole rod set mass filter may be too long to allow the quadrupole mass filter to be scanned quickly enough in order to keep up with the arrival of ions from the ion mobility spectrometer or separator 10. For example, the time for ions having an energy of 3 eV to pass through a 130 mm long quadrupole rod set mass filter is 5.45 $\sqrt{(m/z)}$ µs where m/z is the mass to charge ratio of the ion. Ions having a mass to charge ratio of 200 would, for example, have a transit time of 77 µs. For ions having a mass to charge ratio of 400 the transit time would be 110 µs. Hence, the maximum scan rate is approximately of the order of 100 µs per mass unit or 100 ms per 1000 mass units. This may be too slow to keep up with an ion mobility spectrometer or separator experiment if the drift time of ions having a mass to charge ratio of 1000 through the ion mobility spectrometer or separator 10 was approximately 10 ms.

According to a preferred embodiment a quadrupole mass filter 16 having a faster scan rate and/or an ion mobility spectrometer or separator 10 having longer drift times may be used. The scan rate of the second mass filter 16 may be increased by reducing the length of the second mass filter 16, for example, to 50 mm and/or by increasing the ion energy, for example, to 5 eV. For this arrangement the scan rate would increase by a factor of approximately ×3.

The drift times through the ion mobility spectrometer or separator 10 can also be increased by at least a factor ×3 by increasing the length of the ion mobility spectrometer or separator 10 and reducing the field strength or the amplitude of the travelling wave (i.e. transient DC voltage or potential) applied to the electrodes of the ion mobility spectrometer or separator 10.

According to an embodiment the second mass filter 16 may be scanned at a rate compatible with the arrival of ions from the ion mobility spectrometer or separator 10. This enables the sensitivity of the scanning quadrupole mass filter 16 to be increased for both parent or precursor ion and also fragment, daughter, product or adduct ion mass analysis.

In another mode of operation fragment, daughter, product or adduct ions may be arranged so that they are sufficiently energetic when they enter the ion guide 13 that when they collide with gas molecules present in the ion guide 13 they are caused to fragment into second generation fragment, daughter, product or adduct ions or grand-daughter ions. Subsequent transmission of a specific grand-daughter or second generation ion through the second mass filter 16 and onwards to the ion detector 15 allows the monitoring of a two stage reaction. In certain instances this can provide additional specificity to the measurement.

In another mode of operation fragment, daughter, product or adduct ions may be induced to fragment or react so to as to form second generation fragment, daughter, product or adduct ions in the ion guide 13 and the second mass filter 16 may be set to transmit several different specific ions at a number of different specific ion mobility elution times. This alloys several different second generation fragment, daughter, product or adduct ions to be measured during the course of the ion mobility cycle time. Each second generation fragment, daughter, product or adduct ion may be measured without significant loss in sensitivity, thereby increasing the overall sensitivity. In certain instances these additional measurements can provide a means of further validating the measurement.

In another mode of operation different fragment, daughter, product or adduct ions may be arranged so that they have different kinetic energies when they enter the ion guide 13. The different kinetic energies may be selected such that the efficiency of fragmentation or reaction to form selected second generation fragment, daughter, product or adduct ion is optimised for each fragment ion.

The ion kinetic energy may also be set so that selected fragment, daughter, product or adduct ions enter the ion guide 13 with a low kinetic energy and are not induced to fragment or react. Hence, in one cycle of an ion mobility separation experiment the kinetic energy of fragment, daughter, product or adduct ions may be programmed to several different values and the second mass filter 16 may be programmed to transmit several different species of ions in synchronism. The different species of ions transmitted by the second mass filter 16 to the ion detector 15 in one cycle of an ion mobility experiment may, for example, comprise all first generation fragment, daughter, product or adduct ions or all second generation fragment, daughter, product or adduct ions or a mixture of first and second generation fragment, daughter, product or adduct ions.

The energy of ions entering the ion guide 13 can preferably be controlled, for example, by setting the level of a voltage difference experienced by ions prior to entering the ion guide 13. Since the voltage difference can be switched near instantaneously, the ion guide 13 can, in effect, be considered to be switchable between a relatively high fragmentation or reaction mode of operation and a relatively low fragmentation or reaction mode of operation.

The collision, fragmentation or reaction device 8 may serve the function of an ion trap and may be arranged to store fragment, daughter, product or adduct ions and to release them in pulses to the ion mobility spectrometer or separator 10. In a preferred embodiment the collision, fragmentation or reaction device 8 may comprise an ion guide wherein one or more transient DC voltages or potentials or one or more transient DC voltage or potential waveforms are applied to the electrodes comprising the collision, fragmentation or reaction device 8.

The apertures of the electrodes forming the collision, fragmentation or reaction device 8 are preferably all the same size. Adjacent electrodes are preferably connected to the opposite phases of an AC or RF supply. One or more transient DC voltages or potentials or one or more transient DC voltage or potential waveforms are preferably applied to one or more electrodes of the collision, fragmentation or reaction device 8 in order to form one or more potential hills or barriers. The one or more transient DC voltages or potentials or one or more transient DC voltage or potential waveforms are preferably progressively applied to a succession of electrodes of the collision, fragmentation or reaction device 8 such that the one or more potential hills or barriers preferably move along the axis of the collision, fragmentation or reaction device 8 in the direction in which the ions are to be propelled or driven.

The collision, fragmentation or reaction device 8 is preferably provided in a vacuum chamber which is preferably maintained, in use, at a pressure within the range $10^{-3}$ mbar to $10^{-1}$ mbar. According to less preferred embodiments, the vacuum chamber may be maintained at a pressure greater than $10^{-1}$ mbar up to a pressure at or near 1 mbar. According to other less preferred embodiments, the vacuum chamber may alternatively be maintained at a pressure below $10^{-3}$ mbar. The gas pressure is preferably sufficient to impose collisional damping of ion motion but is preferably not sufficient so as to impose excessive viscous drag on the movement of ions. The amplitude and average velocity of the one or more potential hills or barriers is preferably set such that ions will not slip over a potential hill or barrier. The ions are preferably transported ahead of each travelling potential hill or barrier regardless of their mass, mass to charge ratio or ion mobility.

Ions may be transported in the collision, fragmentation or reaction device 8 and are preferably released as packets to the ion mobility spectrometer or separator 10. The wave cycle time of the collision, fragmentation or reaction device 8 is preferably equal to the cycle time of the ion mobility spectrometer or separator 10. Alternatively, ions may be accumulated and held in a trapping region near the exit of the collision, fragmentation or reaction device 8 and released to the ion mobility spectrometer or separator 10 at the start of each cycle of an ion mobility separation experiment. In this mode of operation the wave cycle time of the collision, fragmentation or reaction device 8 may not match that of the ion mobility spectrometer or separator 10.

The pressure in the collision, fragmentation or reaction device 8 may according to an embodiment be substantially the same as that in the ion guide 13. In a preferred embodiment the collision, fragmentation or reaction device 8 and the ion guide 13 are preferably located in the same vacuum chamber. The ion mobility spectrometer or separator 10 may be contained or otherwise housed within an inner chamber positioned within the vacuum chamber housing the collision, fragmentation or reaction device 8 and the ion guide 13. A collision gas, preferably nitrogen or argon, may be leaked or supplied into the inner chamber in order to maintain the inner chamber at a preferred pressure between 0.1 and 10 mbar. The collision gas may leak into the outer chamber through an entrance and an exit aperture of the inner chamber. The outer chamber is preferably pumped such as to maintain a pressure in the outer chamber within the range 0.001 and 0.01 mbar.

Figure 4:
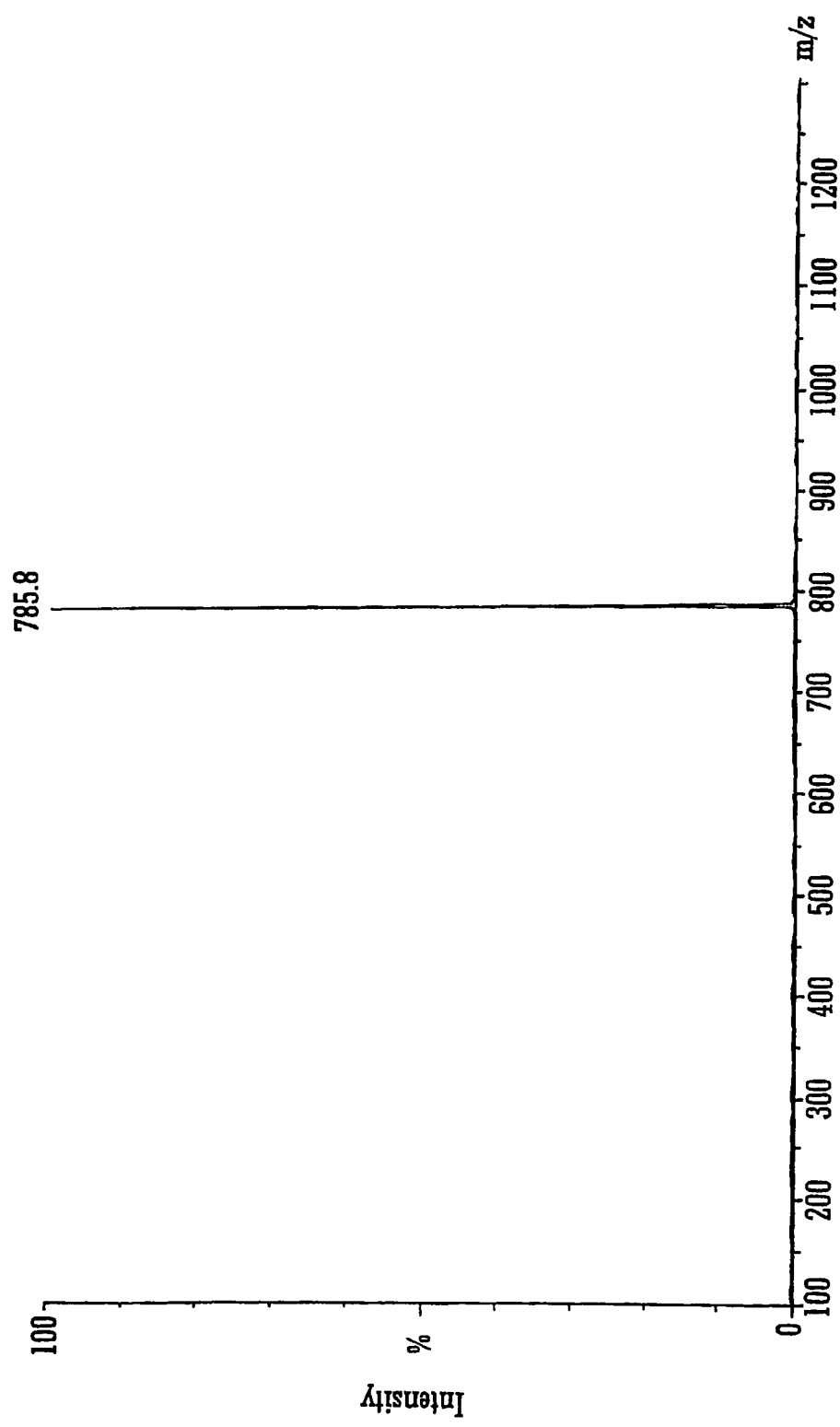
FIG. 4 shows an Electrospray mass spectrum for the peptide Glu-Fibrinopeptide B.

FIG. 4 shows a mass spectrum of the peptide Glu-Fibrinopeptide B produced by ionising a sample using an Electrospray ion source. It can be seen that the most abundant ion is the doubly protonated ion M+2H 2+ having a mass to charge ratio of 785.8

Figure 5:
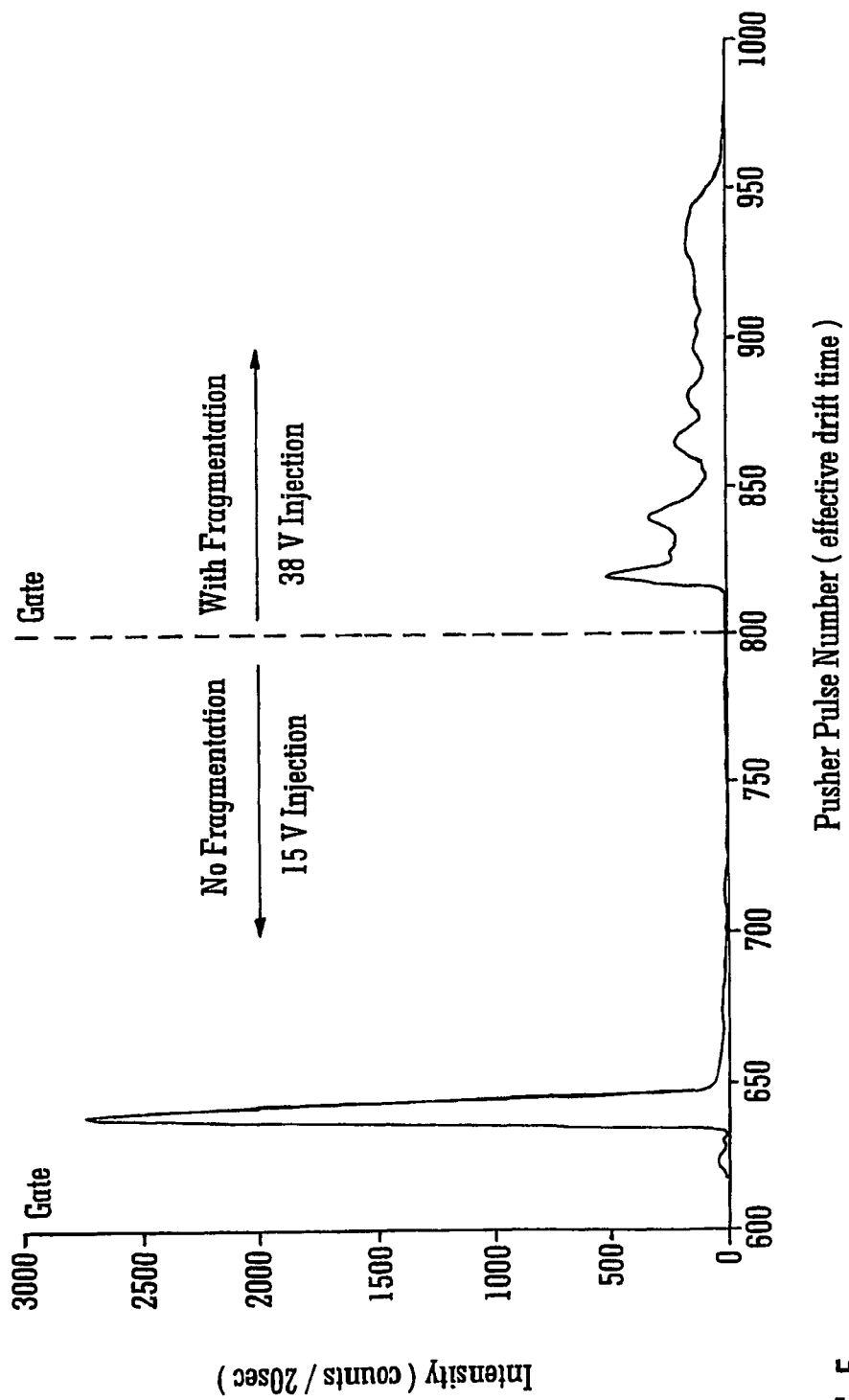
FIG. 5 shows an ion mobility spectrum of the peptide Glu-Fibrinopeptide B and an ion mobility spectrum of the fragments of the peptide Glu-Fibrinopeptide B.

FIG. 5 shows an ion mobility spectrum initially of the peptide Glu-Fibrinopeptide B and then subsequently of the fragments of the peptide. The doubly protonated parent ion having a mass to charge ratio of 785.8 was initially arranged to be transmitted by a first quadrupole rod set mass filter 7 and was injected into a collision, fragmentation or reaction device 8 which comprised a collision cell. An energy voltage of 15V was applied to the collision cell. The ions were arranged to emerge from the collision cell and were passed to an ion mobility spectrometer or separator 10. The ions were then temporally separated according to their ion mobility in an ion mobility spectrometer or separator 10. A 7 V potential hill travelling at 300 m/sec was repeatedly translated along the length of the ion mobility spectrometer or separator 10 in order to separate ions temporally. The ion mobility spectrometer or separator 10 was maintained at a pressure of 0.2 mbar. The ions were detected with an ion detector 15. The peptide ion was then fragmented. In order to fragment the peptide ion a potential difference of 38 V was maintained so that ions were energetically accelerated in the collision cell. An ion mobility spectrum of the resulting fragment ions is also shown in FIG. 5.

Figure 6:
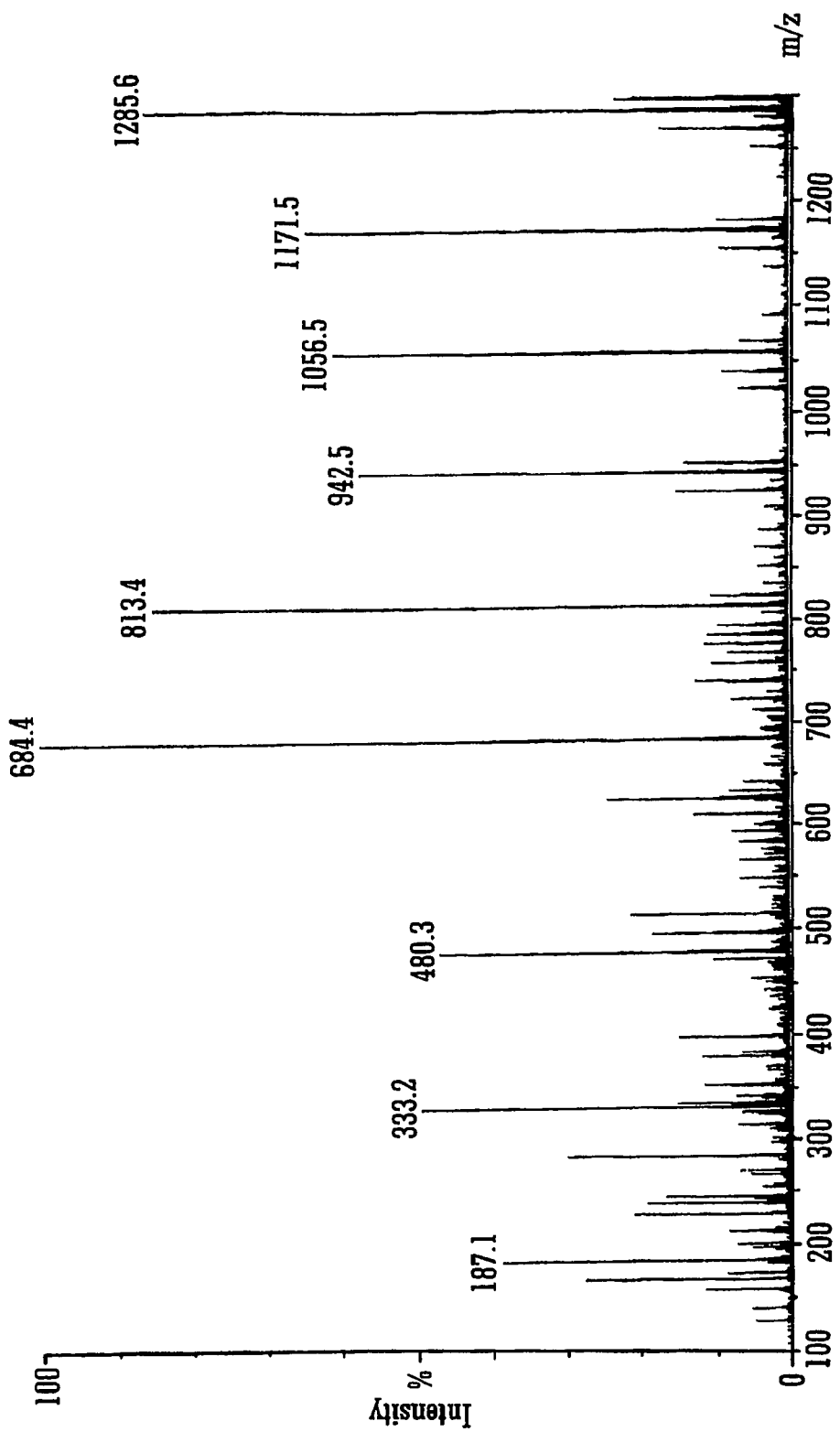
FIG. 6 shows a mass spectrum of the fragment ions resulting from fragmentation of the doubly charged ion of the peptide Glu-Fibrinopeptide B.

FIG. 6 shows a normal mass spectrum of the fragment ions resulting from the fragmentation of the doubly charged protonated ion of the peptide Glu-Fibrinopeptide B.

Figure 7:
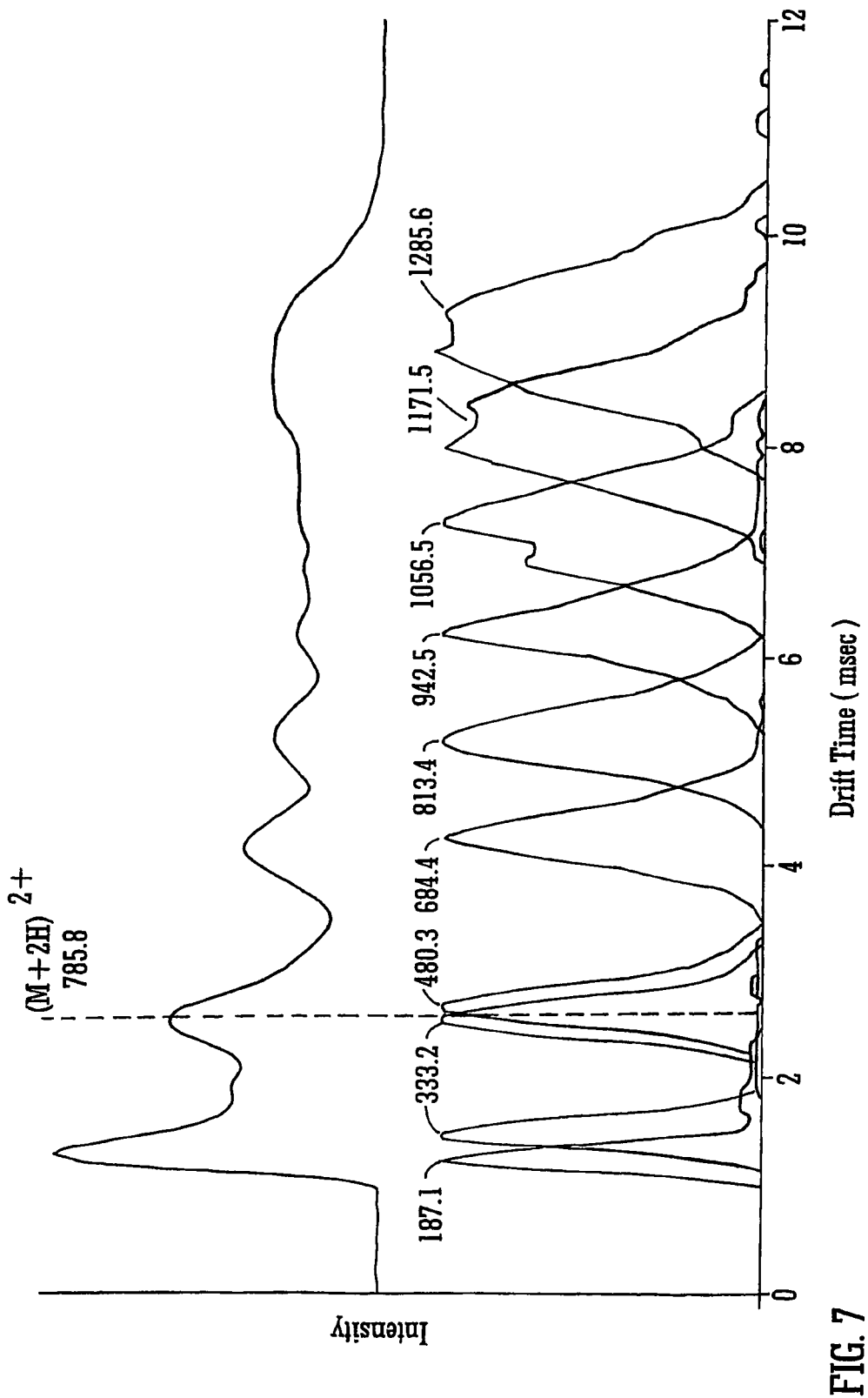
FIG. 7 shows an ion mobility spectrum of all the fragment ions from the doubly charged ion of the peptide Glu-Fibrinopeptide B and an ion mobility spectrum showing a number of specific fragment ions from the doubly charged ion of the peptide Glu-Fibrinopeptide B.

The upper curve of FIG. 7 shows an ion mobility spectrum for all of the fragment ions resulting from the fragmentation of the doubly charged ion of the peptide Glu-Fibrinopeptide B. The lower curve of FIG. 7 shows overlapped ion mobility spectra for various specific fragment ions which resulted from the fragmentation of the doubly charged ion of the same peptide. The second quadrupole mass filter 16 was set to transmit ions having just the mass to charge ratios specified in order to generate each individual ion mobility spectrum shown in FIG. 7. The duration of the ion mobility experiment was 12 ms and each individual ion mobility spectrum was recorded over the full duration of the ion mobility experiment. It can be seen from this data that the second quadrupole mass filter 16 could be set so as to transmit several different fragment or daughter ions at different stages or times during the course of an ion mobility experiment.

The embodiment illustrated in FIG. 3 may also be used to conduct a parent or precursor ion scanning experiment. In a conventional mass spectrometer the second quadrupole rod set mass filter would be set to transmit a specific characteristic fragment or daughter ion whilst the first quadrupole rod set mass filter would be scanned so as to sequentially transmit specific parent or precursor ions to a gas collision cell for fragmentation. When a specific fragment or daughter ion is detected then the mass to charge ratio of the corresponding parent or precursor ion transmitted by the first quadrupole mass filter would be recorded. This approach has proved particularly useful in the analysis of protein post-translational modifications, such as phosphorylation and glycosylation. However, since it is necessary to scan the first quadrupole rod set mass filter the sampling duty cycle can be quite low, commonly less than 1%. Consequently the sensitivity is low.

A mass spectrometer according to the embodiment shown in FIG. 3 can be operated in a mode of operation wherein all the ions are transmitted through the first quadrupole rod set mass filter 7 and are received and accumulated in the collision, fragmentation or reaction device 8 without being caused to fragment or react. The stored parent or precursor ions are then preferably periodically released in a pulse from the collision, fragmentation or reaction device 8 and are then preferably temporally separated in the ion mobility spectrometer or separator 10. The parent or precursor ions are then preferably fragmented or reacted in the ion guide 13 arranged downstream of the ion mobility spectrometer or separator 10 as the ions enter the ion guide 13. The resulting fragment, daughter, product or adduct ion are then preferably transmitted to the second mass filter 16 which is preferably arranged to transmit only certain specific fragment, daughter, product or adduct ions. This embodiment provides a means of parent or precursor ion scanning having a duty cycle of substantially 100%. It will be appreciated that this is particularly advantageous compared to conventional arrangements which exhibit a very low duty cycle, for example, when scanning a conventional triple quadrupole mass spectrometer.

Other embodiments of the present invention are also contemplated wherein the AC or RF voltage supplied to electrodes forming the ion mobility spectrometer or separator 10 and/or the ion guide 13 downstream of the ion mobility spectrometer or separator 10 and/or the collision, fragmentation or reaction device 8 upstream of the ion mobility spectrometer or separator 10 may comprise a non-sinusoidal voltage and may, for example, comprise a square wave.

According to an embodiment the collision, fragmentation or reaction device 8, the ion mobility spectrometer or separator 10 and the ion guide 13 may comprise an ion tunnel ion guide i.e. a plurality of electrodes wherein each electrode has an aperture therein through which ions are transmitted. The electrodes preferably have substantially similar sized apertures. The electrodes may comprise essentially a square or rectangular plate or a ring. The apertures are preferably circular. The collision, fragmentation or reaction device 8 and/or the ion mobility spectrometer or separator 10 and/or the ion guide 13 may comprise at least 10, 20, 30, 40, 50, 60, 70, 80, 90 or 100 electrodes of which at least 60%, 65%, 70%, 75%, 80%, 85%, 90% or 95% have apertures which are substantially the same size or area.

Although the present invention has been described with reference to preferred embodiments, it will be understood by those skilled in the art that various changes in form and detail may be made without departing from the scope of the invention as set forth in the accompanying claims.

The invention claimed is:

1. A mass spectrometer comprising:
a first collision, fragmentation or reaction device arranged and adapted to fragment or react ions and to produce product, daughter, adduct or fragment ions; and
an ion mobility spectrometer or separator arranged downstream of said first collision, fragmentation or reaction device, said ion mobility spectrometer or separator being arranged to temporally separate product, daughter, adduct or fragment ions according to their ion mobility which emerge from or which have been transmitted from said first collision, fragmentation or reaction device; wherein said collision, fragmentation or reaction device is configured to pulse ions out of said collision, fragmentation or reaction device and into or towards said ion mobility spectrometer or separator; and
a mass filter arranged downstream of said ion mobility spectrometer or separator.

2. A mass spectrometer as claimed in claim 1, wherein said collision, fragmentation or reaction device is arranged and adapted to trap ions within said collision, fragmentation or reaction device in a mode of operation.

3. A mass spectrometer as claimed in claim 1, further comprising a mass filter or mass analyser arranged upstream of said first collision, fragmentation or reaction device.

4. A mass spectrometer as claimed in claim 1, wherein said first collision, fragmentation or reaction device comprises:
(i) a multipole rod set or a segmented multipole rod set;
(ii) an ion tunnel or ion funnel; or
(iii) a stack or array of planar, plate or mesh electrodes.

5. A mass spectrometer as claimed in claim 1, further comprising first acceleration means arranged and adapted to accelerate ions into said first collision, fragmentation or reaction device wherein in a mode of operation at least 5%, 10%, 15%, 20%, 25%, 30%, 35%, 40%, 45%, 50° A, 55%, 60%, 65%, 70%, 75%, 80%, 85%, 90%, 95% or 100% of said ions are caused to fragment or react upon entering said first collision, fragmentation or reaction device.

6. A mass spectrometer as claimed in claim 1, further comprising a control system arranged and adapted to switch or repeatedly switch the potential difference through which ions pass prior to entering said first collision, fragmentation or reaction device between a relatively high fragmentation or reaction mode of operation wherein ions are substantially fragmented or reacted upon entering said first collision, fragmentation or reaction device and a relatively low fragmentation or reaction mode of operation wherein substantially fewer ions are fragmented or reacted or wherein substantially no ions are fragmented or reacted upon entering said first collision, fragmentation or reaction device.

7. A mass spectrometer as claimed in claim 1, wherein said first collision, fragmentation or reaction device is arranged and adapted to receive a beam of ions and to convert or partition said beam of ions such that at least 1, 2, 3, 4, 5, 6, 7, 8, 9, 10, 11, 12, 13, 14, 15, 16, 17, 18, 19 or 20 separate groups or packets of ions are confined or isolated in said first collision, fragmentation or reaction device at any particular time, and wherein each group or packet of ions is separately confined or isolated in a separate axial potential well formed in said first collision, fragmentation or reaction device.

8. A mass spectrometer as claimed in claim 1, further comprising a second collision, fragmentation or reaction device, wherein said second collision, fragmentation or reaction device is arranged downstream of said ion mobility spectrometer or separator.

9. A mass spectrometer as claimed in claim 8, wherein said second collision, fragmentation or reaction device comprises a plurality of axial segments or at least 5, 10, 15, 20, 25, 30, 35, 40, 45, 50, 55, 60, 65, 70, 75, 80, 85, 90, 95 or 100 axial segments.

10. A mass spectrometer as claimed in claim 8, further comprising transient DC voltage means arranged and adapted to apply one or more transient DC voltages or potentials or one or more transient DC voltage or potential waveforms to electrodes forming said second collision, fragmentation or reaction device in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of said second collision, fragmentation or reaction device.

11. A mass spectrometer as claimed in claim 8, further comprising AC or RF voltage means arranged and adapted to apply two or more phase-shifted AC or RF voltages to electrodes forming said second collision, fragmentation or reaction device in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of said second collision, fragmentation or reaction device.

12. A mass spectrometer as claimed in claim 8, wherein said second collision, fragmentation or reaction device further comprises a plurality of electrodes and AC or RF voltage means arranged and adapted to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of said plurality of electrodes of said second collision, fragmentation or reaction device in order to confine ions radially within said second collision, fragmentation or reaction device.

13. A mass spectrometer as claimed in claim 8, further comprising acceleration means arranged and adapted to accelerate ions emerging from said ion mobility spectrometer or separator into said second collision, fragmentation or reaction device and wherein in a mode of operation at least 5%, 10%, 15%, 20%, 25%, 30%, 35%, 40%, 45%, 50%, 55%, 60%, 65%, 70%, 75%, 80%, 85%, 90%, 95% or 100% of said ions are caused to fragment or react upon entering said second collision, fragmentation or reaction device.

14. A mass spectrometer as claimed in claim 13, wherein said acceleration means is arranged and adapted to progressively vary or increase the kinetic energy of ions emerging from said ion mobility spectrometer or separator as they are transmitted to said second collision, fragmentation or reaction device.

15. A mass spectrometer as claimed in claim 13, further comprising a control system arranged and adapted to switch or repeatedly switch the potential difference through which ions pass prior to entering said second collision, fragmentation or reaction device between a relatively high fragmentation or reaction mode of operation wherein ions are substantially fragmented or reacted upon entering said second collision, fragmentation or reaction device and a relatively low fragmentation or reaction mode of operation wherein substantially fewer ions are fragmented or reacted or wherein substantially no ions are fragmented or reacted upon entering said second collision, fragmentation or reaction device.

16. A mass spectrometer as claimed in claim 8, wherein said second collision, fragmentation or reaction device is arranged and adapted to receive a beam of ions from said ion mobility spectrometer or separator and to convert or partition said beam of ions such that at least 1, 2, 3, 4, 5, 6, 7, 8, 9, 10, 11, 12, 13, 14, 15, 16, 17, 18, 19 or 20 separate groups or packets of ions are confined or isolated in said second collision, fragmentation or reaction device at any particular time, and wherein each group or packet of ions is separately confined or isolated in a separate axial potential well formed in said second collision, fragmentation or reaction device.

17. A mass spectrometer as claimed in claim 8, wherein said second collision, fragmentation or reaction device is arranged and adapted to retain or confine or partition ions emerging from said ion mobility spectrometer or separator and to translate ions in one or more groups or packets of ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of said second collision, fragmentation or reaction device whilst either: (i) substantially maintaining the order or fidelity in which ions emerge from said ion mobility spectrometer or separator; or (ii) substantially maintaining the composition of ions as one or more groups or packets of ions are translated along said second collision, fragmentation or reaction device.

18. A mass spectrometer as claimed in claim 1, wherein said ion mobility spectrometer or separator comprises a gas phase electrophoresis device.

19. A mass spectrometer as claimed in claim 1, wherein said ion mobility spectrometer or separator comprises a plurality of axial segments or at least 5, 10, 15, 20, 25, 30, 35, 40, 45, 50, 55, 60, 65, 70, 75, 80, 85, 90, 95 or 100 axial segments.

20. A mass spectrometer as claimed in claim 1, further comprising DC voltage means for maintaining a substantially constant DC voltage gradient along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of said ion mobility spectrometer or separator in order to urge at least some ions along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of said ion mobility spectrometer or separator.

21. A mass spectrometer as claimed in claim 1, further comprising transient DC voltage means arranged and adapted to apply one or more transient DC voltages or potentials or one or more transient DC voltage or potential waveforms to electrodes forming said ion mobility spectrometer or separator in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of said ion mobility spectrometer or separator.

22. A mass spectrometer as claimed in claim 1, further comprising AC or RF voltage means arranged and adapted to apply two or more phase-shifted AC or RF voltages to electrodes forming said ion mobility spectrometer or separator in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of said ion mobility spectrometer or separator.

23. A mass spectrometer as claimed in claim 1, further comprising an ion detector.

24. A mass spectrometer as claimed in claim 1, wherein said mass filter is arranged to transmit only specific product, daughter, adduct or fragment ions at one time.

25. A mass spectrometer as claimed in claim 24, wherein said mass filter is scanned so as to transmit different specific product, daughter, adduct or fragment ions at different times.

26. A mass spectrometer as claimed in claim 1, wherein said ion mobility spectrometer or separator is configured to delay some of the product, daughter, adduct or fragment ions to produce delayed ions and wherein said mass filter is configured to analyse only specific product, daughter, adduct or fragment ions within a certain range of mass to charge ratios without discarding the delayed ions.

27. A mass spectrometer as claimed in claim 1, wherein said mass filter is selected from the group consisting of: a quadrupole rod set mass filter, a Wein filter and a magnetic sector mass filter.

28. A mass spectrometer comprising:
a first mass filter or mass analyser;
an ion mobility spectrometer or separator, said ion mobility spectrometer or separator being arranged downstream of said first mass filter or mass analyser;
a first collision, fragmentation or reaction device arranged upstream of said ion mobility spectrometer or separator and downstream of said first mass filter or mass analyser;
means for causing ions to fragment or react in said first device to produce fragment or product ions; and
a second mass filter or mass analyser arranged downstream of said ion mobility spectrometer or separator; wherein said second mass filter or mass analyser is scanned in synchronism with said ion mobility spectrometer or separator.

29. A mass spectrometer as claimed in claim 28, wherein in a first mode of operation said first mass filter or mass analyser is operated in a substantially non-resolving or ion guiding mode of operation.

30. A mass spectrometer as claimed in claim 28, wherein in a mode of operation said first mass filter or mass analyser or said second mass filter or mass analyser is operated in a resolving or mass filtering mode of operation.

31. A mass spectrometer as claimed in claim 28, wherein in a mode of operation said first mass filter or mass analyser is scanned.

32. A mass spectrometer as claimed in claim 28, wherein in a mode of operation said first mass filter or mass analyser is scanned in synchronism with said ion mobility spectrometer or separator.

33. A mass spectrometer as claimed in claim 28, wherein in a mode of operation said first mass filter or mass analyser is scanned in synchronism with said second mass filter or mass analyser.

34. A mass spectrometer as claimed in claim 28, wherein said first collision, fragmentation or reaction device comprises a plurality of axial segments or at least 5, 10, 15, 20, 25, 30, 35, 40, 45, 50, 55, 60, 65, 70, 75, 80, 85, 90, 95 or 100 axial segments.

35. A mass spectrometer as claimed in claim 28, further comprising transient DC voltage means arranged and adapted to apply one or more transient DC voltages or potentials or one or more transient DC voltage or potential waveforms to electrodes forming said first collision, fragmentation or reaction device in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of said first collision, fragmentation or reaction device.

36. A mass spectrometer as claimed in claim 28, further comprising AC or RF voltage means arranged and adapted to apply two or more phase-shifted AC or RF voltages to electrodes forming said first collision, fragmentation or reaction device in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of said first collision, fragmentation or reaction device.

37. A mass spectrometer as claimed in claim 28, wherein said mass spectrometer is arranged to scan said second mass filter or mass analyser in synchronism with said ion mobility spectrometer or separator, wherein a scan law or scan function of the second mass filter or mass analyser is arranged so as to match a relationship between the mass to charge ratio of an ion and an exit time of the ions from the ion mobility spectrometer or separation such that a substantial number of fragment or product ions exiting the ion mobility spectrometer or separator are subsequently transmitted through the second mass filter or mass analyser.

38. A method of mass spectrometry comprising:
  fragmenting or reacting ions in a first collision, fragmentation or reaction device to produce product, daughter, adduct or fragment ions;
  pulsing ions out of said collision, fragmentation or reaction device and into or towards an ion mobility spectrometer or separator;
  temporally separating product, daughter, adduct or fragment ions according to their ion mobility which emerge from or which have been transmitted from said first collision, fragmentation or reaction device in said ion mobility spectrometer or separator; and
  mass filtering ions in a mass filter arranged downstream of said ion mobility spectrometer or separator.

39. A method as claimed in claim 38, wherein said mass filter transmits only specific product, daughter, adduct or fragment ions at one time.

40. A method as claimed in claim 39, wherein said mass filter is scanned so as to transmit different specific product, daughter, adduct or fragment ions at different times.

41. A method of mass spectrometry comprising:
  mass filtering or mass analysing ions in a first mass filter or mass analyser;
  fragmenting or reacting ions in a first collision, fragmentation or reaction device arranged downstream of said first mass filter or mass analyser to produce fragment or product ions;
  temporally separating ions in an ion mobility spectrometer or separator, said ion mobility spectrometer or separator being arranged downstream of said collision, fragmentation or reaction device; and
  mass filtering or mass analysing ions in a second mass filter or mass analyser arranged downstream of said ion mobility spectrometer or separator; wherein said second mass filter or mass analyser is scanned in synchronism with said ion mobility spectrometer or separator.

42. A method as claimed in claim 41, wherein said second mass filter or mass analyser is scanned in synchronism with said ion mobility spectrometer or separator, and wherein a scan law or scan function of the second mass filter or mass analyser matches a relationship between the mass to charge ratio of an ion and an exit time of the ions from the ion mobility spectrometer or separator such that a substantial number of fragment or product ions exiting the ion mobility spectrometer or separator are subsequently transmitted through the second mass filter or mass analyser.

\* \* \* \* \*